(12) United States Patent
Paukshto et al.

(10) Patent No.: US 11,013,826 B2
(45) Date of Patent: May 25, 2021

(54) BIOCOMPOSITES AND METHODS OF MAKING THE SAME

(71) Applicant: Fibralign Corporation, Union City, CA (US)

(72) Inventors: Mikhail Vitoldovich Paukshto, Foster City, CA (US); David Harwood McMurtry, Felton, CA (US); Tatiana Zaitseva, San Jose, CA (US)

(73) Assignee: Fibralign Corporation, Union City, CA (US)

( * ) Notice: Subject to any disclaimer, the term of this patent is extended or adjusted under 35 U.S.C. 154(b) by 0 days.

(21) Appl. No.: 16/138,817

(22) Filed: Sep. 21, 2018

(65) Prior Publication Data

US 2019/0015549 A1    Jan. 17, 2019

Related U.S. Application Data

(63) Continuation-in-part of application No. 13/925,005, filed on Jun. 24, 2013, now Pat. No. 10,086,079, which is a continuation-in-part of application No. 12/539,563, filed on Aug. 11, 2009, now Pat. No. 8,513,382.

(60) Provisional application No. 61/190,770, filed on Sep. 3, 2008, provisional application No. 61/136,066, filed on Aug. 11, 2008, provisional application No. 61/690,306, filed on Jun. 25, 2012.

(51) Int. Cl.
| | |
|---|---|
| *A61L 27/24* | (2006.01) |
| *A61L 27/38* | (2006.01) |
| *A61L 27/54* | (2006.01) |
| *C12N 5/077* | (2010.01) |
| *C12N 5/0775* | (2010.01) |
| *D01D 5/24* | (2006.01) |
| *D01D 5/247* | (2006.01) |
| *D01D 5/00* | (2006.01) |
| *A61L 27/56* | (2006.01) |
| *D01F 4/00* | (2006.01) |

(52) U.S. Cl.
CPC .............. *A61L 27/24* (2013.01); *A61L 27/38* (2013.01); *A61L 27/3804* (2013.01); *A61L 27/54* (2013.01); *A61L 27/56* (2013.01); *C12N 5/0656* (2013.01); *C12N 5/0662* (2013.01); *C12N 5/0663* (2013.01); *D01D 5/00* (2013.01); *D01D 5/24* (2013.01); *D01D 5/247* (2013.01); *A61L 2430/30* (2013.01); *A61L 2430/32* (2013.01); *C12N 2533/54* (2013.01); *C12N 2537/10* (2013.01); *D01F 4/00* (2013.01); *D10B 2211/06* (2013.01); *D10B 2401/063* (2013.01); *D10B 2401/12* (2013.01); *D10B 2509/00* (2013.01)

(58) Field of Classification Search
None
See application file for complete search history.

(56) References Cited

U.S. PATENT DOCUMENTS

| | | | | |
|---|---|---|---|---|
| 8,492,332 | B2 * | 7/2013 | Paukshto | A61L 27/24 514/7.2 |
| 10,086,079 | B2 * | 10/2018 | Paukshto | A61K 47/42 |

* cited by examiner

*Primary Examiner* — Anand U Desai
(74) *Attorney, Agent, or Firm* — DLA Piper LLP (US)

(57) ABSTRACT

In general, the present invention is related to biopolymer and biocomposite materials and structures, and methods of making and using the same. In some embodiments, the present invention is directed to oriented collagen based biocomposite materials and structures, and methods of making.

19 Claims, 15 Drawing Sheets

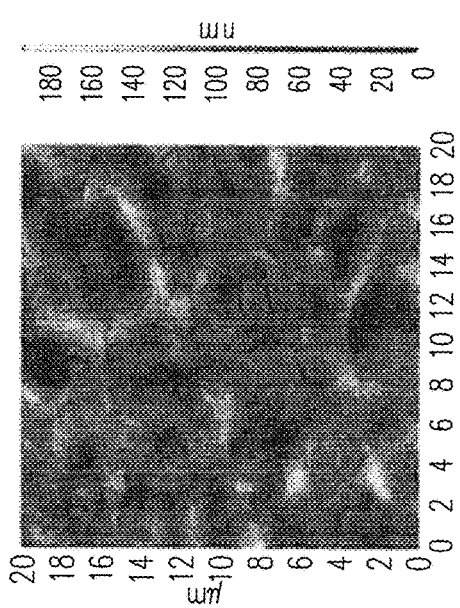
FIG. 3A Cornea-like
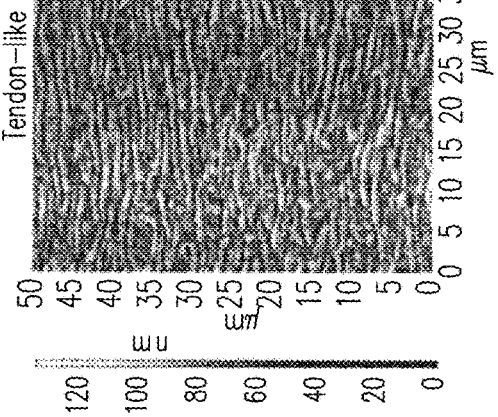
FIG. 3B Vertical fibrils
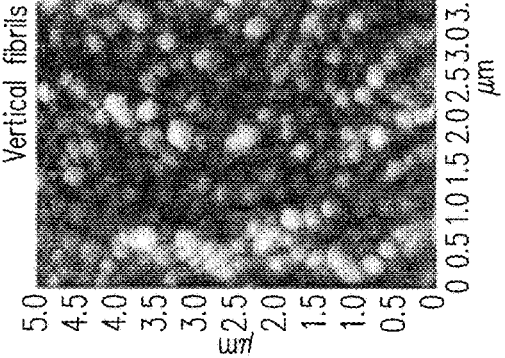
FIG. 3C Tendon-like
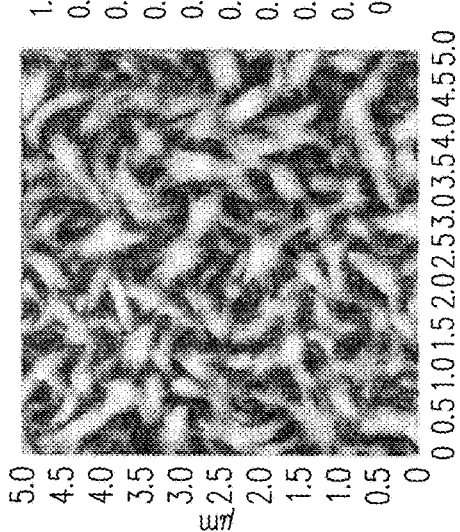
FIG. 3D Skin-like
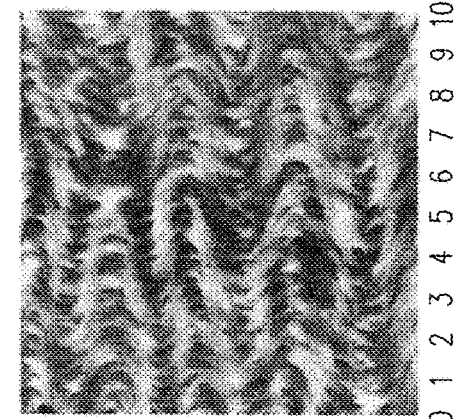
FIG. 3E Heart valve-like
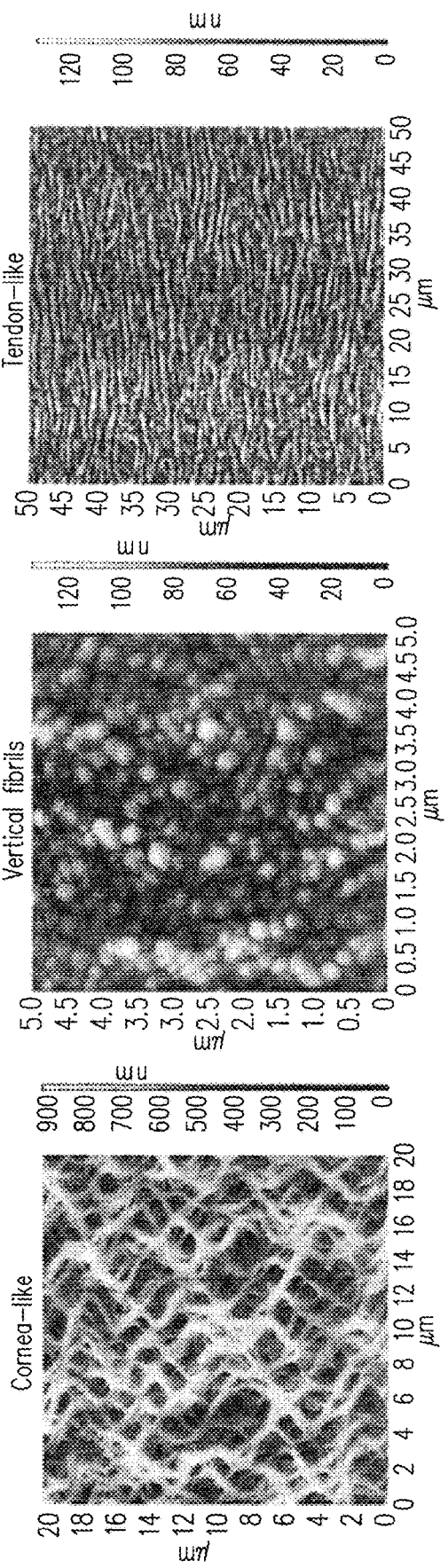
FIG. 3F B-membrane SEM of rat-tail tendon AFM of tendon-like collagen ribbon Tendon-like Woven Skin-like Aligned-braided a) Tendon-porcine heart valve, (Alan Freed, ASME 2005)

b) CollEngin tendon-like collegen matrix

Pseudo-fiber

Cells seeded on oriented collagen pseudo-fiber proliferate and migrate from the pseudo-fiber after 5 days

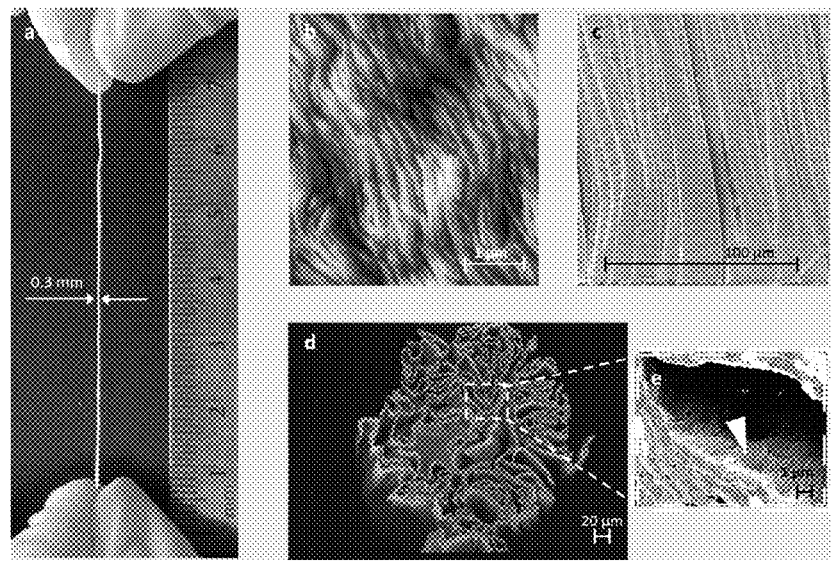
FIG. 18A – E
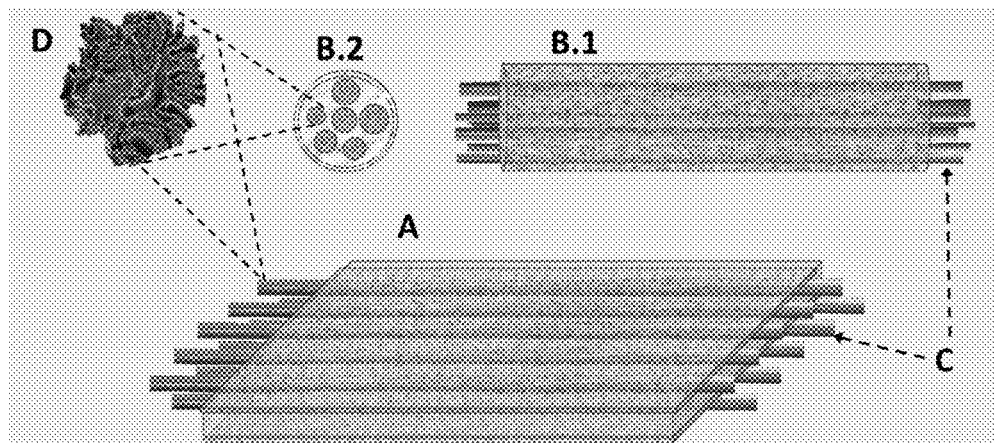
FIG. 19

BIOCOMPOSITES AND METHODS OF MAKING THE SAME

CROSS REFERENCE TO RELATED APPLICATIONS

This application is a Continuation-in-Part of U.S. patent application Ser. No. 13/925,005, filed on Jun. 24, 2013, entitled "Biocomposites And Methods Of Making The Same" which is a Continuation-in-Part of U.S. patent application Ser. No. 12/539,563, filed on Aug. 11, 2009, entitled "Biocomposites And Methods Of Making The Same" now U.S. Pat. No. 8,513,382 which claims the benefit of U.S. Provisional Patent application Ser. No. 61/136,066 filed on Aug. 11, 2008, entitled "Biocomposites And Methods Of Making The Same" and U.S. Provisional Patent application Ser. No. 61/190,770, filed on Sep. 3, 2008, entitled "Direct Incorporation Of Orthovanadate And Other Factors Into Collagen Matrices To Enhance Fibril Stability A Well As To Enhance Cellular Attachment, Migration, Growth And Differentiation" the disclosures of all of which are incorporated by reference herein in their entireties. U.S. patent application Ser. No. 13/925,005 also claims the benefit of, and priority to, U.S. Provisional Patent application Ser. No. 61/690,306, filed on Jun. 25, 2012, entitled "Medical Device and its Delivery Method" the entire disclosure of which is hereby incorporated by reference.

FIELD OF THE INVENTION

In general, the present invention is related to biopolymer and biocomposite materials and structures, and methods of making and using the same. In some embodiments, the present invention is directed to oriented collagen based biocomposite materials and structures, and methods of making.

BACKGROUND OF THE INVENTION

Collagen gels, bandages, sponges and fibers have been used as carrier for stem cells. Collagen is a natural protein present in many tissues. It supplies tensile strength to the tissues as well as providing attachment sites for cells to bind, migrate and proliferate. However, collagen gels and pulverized collagen lack tensile strength and tend to dissipate in the tissue under pressure and thus are not well suited to the task of maintaining cells in defined locations.

Collagen can be isolated in pure form from a variety of tissues as a soluble protein which can be reconstituted into fibers. In general, fibers lack the superstructure they exhibit in different tissues. This has limited the success of using collagen in many medical applications.

Tissue damage to heart, striated muscle, skin, bone and cartilage, spinal cord, etc. often progresses and causes the breakdown of normal surrounding tissue increasing the area damaged and seriously impairing tissue function. Current concepts suggest that various factors or cells could be introduced into the damaged area by direct injection and prevent further damage and even restore the damaged area. Indeed, preclinical as well as clinical trials have shown improved heart function when mesenchymal stem cells are injected into the site of tissue damage. However, such studies have also shown that significant amounts of the injected cells leak out of the tissue and most of the cells remaining rapidly die. Thus there is a need for devices which allows delivery of various types of cells to specific sites in damaged tissue and maintain their survival and expansion. However, the physical properties of different tissues vary strikingly (compare heart muscle with striated muscle with skin or spinal cord. Thus, delivery vehicles should have sufficient strength to allow them to be placed in a specific tissue without causing alterations in tissue function due to poorly matched physical factors. This calls for materials whose physical properties are suitable for the tissue in which they are to be used. Also, cells require factors and surfaces to support their survival, migration and production of specific repair factors. In brief, the treatment of damaged tissues should be improved by novel devices which would deliver and maintain stem and other cells in specific sites to allow them to survive and produce factors that sustain tissue at risk.

Tendon and ligament injuries are among the most common health problems affecting the adult population. It is estimated that 175,000 Anterior Cruciate Ligament (ACL) reconstructions were performed in the year 2000 in the United States at a cost of more than $2 billion. There are 50,000 patients requiring surgical repair of rotator cuff and 5 million new cases of tennis elbow each year in the United States alone. In addition, 11% of regular runners suffer from Achilles tendinopathy. In 2000, treatments for shoulder pain cost the United States government up to $7 billion and the total cost for tendon and ligament injury has been estimated at $30 billion annually; see Chen, J., Xu J., Wang A., Zheng M., 2009. Scaffolds for tendon and ligament repair: review of the efficacy of commercial products. Expert Rev. Med. Devices. 6. 1:61-73.

Current methods to repair tendon and ligaments of the hand and foot have had only limited success. In some cases, the joints are immobilized for four weeks while scar tissue builds up. This scar tissue, which has poor mechanical properties, must assume the function of the original tendon/ligament but has a high rate of failure. In other cases non-absorbable sutures anchored to bone are used. These sutures lack the appropriate elasticity and often evoke an immune response. In other cases, repair is not possible and the replacement procedures available have various limitations.

Current clinical and research practice utilizes animal and human grafts as the primary material in daily clinical practice to repair tendon and ligament defects. Biological substitutes include autografts, allografts, and xenografts.

Autologous grafts of patellar tendon and hamstring tendons are considered the "gold standard" in tissue repair and are usually preferred to avoid rejection. However, these autografts suffer from a number of disadvantages. For example, autografts require additional surgery on the patient which may cause donor site morbidity, increased recovery time, and/or possible pain at the harvesting site plus harvest site infection, nerve injury, and patellar fracture. An additional disadvantage in the use of the hamstring tendon for ACL reconstruction is the lack of efficient tendon-bone healing, which affects patient recovery due to instability of the tendon-bone interface.

Allografts are obtained from tendons, dermis and other tissues of cadavers. Xenografts are harvested from animal tendons, small intestine submucosa, dermis and skin, and pericardium. Allografts and xenografts are primarily composed of type I collagen with similar mechanical properties to human tendons. However, allo- and xenografts can potentially transmit disease or infection, and may elicit an unfavorable immunogenic response from the host.

Synthetic grafts exhibit excellent short-term results but the long-term clinical outcome is poor, with a failure rate of 40 to 78% from fragmentation, stress shielding of new tissue, fatigue, creep, and wear debris, which can eventually lead to arthritis and synovitis.

Current cell-seeding techniques include: a) delivering cell-gel composites into the region of the scaffold and b) delivering cell suspensions into scaffolds in a static or dynamic situation. However, there are some disadvantages to these techniques, such as the low efficiency of cell attachment to dense fibrous matrix or scaffolds and the weak mechanical strength of gel systems. These disadvantages make it very difficult to seed a significant number of cells on dense tissue grafts. Thus the limitations of current technology prohibit the use of stem cells to improve the efficiency of large tissue grafts for tissue repair. To address these limitations partial thickness incisions and ultrasonication were developed to allow the seeded cells to infiltrate the tendon in culture prior to implantation. Without incisions or ultrasonication, extrinsic cells seeded onto the tendon surface have difficulty penetrating the tendon. However, with incision and ultrasonication, the mechanical strength of the grafts is reduced which limits the potential of clinical application.

Several research groups have attempted to tissue engineer neo-ligaments in vitro for tendon and ligament replacements as described in Hairfield-Stein M. et al. 2007. Development of Self-Assembled, Tissue-Engineered Ligament from Bone Marrow Stromal Cells. Tissue Engineering. 13. 4:703-710. One of the first promising results in this direction has been published by Goldstein J D et al. in Goldstein, J D, et al. 1989. Development of a Reconstituted Collagen Tendon Prosthesis. The Journal of Bone and Joins Surgery. 71. A. 8: 1183-1191; and Dunn et al. Dunn, MG. et al. 1992. Anterior cruciate ligament reconstruction using a composite collagenous prosthesis. A biomechanical & histological rabbit study. Am J Sports Med. 20. 507-515. Constructed scaffolds of collagen fibers are bundled in different configurations with and without a collagen gel to hold them together. Dunn et al. and other groups used collagen scaffolds with and without seeded cells. The main problems of this approach have been: a) the rate of degradation of scaffold collagen was higher than the rate of newly synthesized collagen causing the neo-ligament to fail to support in vivo loading; and b) the cost of production was too high and reproducibility was low.

To reduce the rate of degradation, several research groups have used silk and other synthetic materials. This solved the enzymatic degradation problem but generated other problems including immune reactions, fibrosis, and wear debris. Attempts to eliminate extracellular matrix scaffolds have led to a new approach of so-called "functional tissue-engineering" or "spontaneous 3-dimensional tissue development" as described in Calve, S., Dennis R G, Kosnik P E, Baar K, Grosh K, Arruda E M. 2004. Engineering of functional tendon. Tissue Engineering. 10, 755-761. This method does not rely as heavily upon the material properties of pre-existing artificial or biological scaffolds which limit the physiologic or mechanical properties of the newly formed tissue. Rather media like collagen gels, fibrin gels, Matrigel, or synthetic gels are employed to orchestrate the formation of the newly formed tissue. Chen et al in Chen X, Zou X H, Yin G L, Ouyang H W. 2009. Tendon tissue engineering with mesenchymal stem cells and biografts: an option for large tendon defects? Frontiers in Bioscience. S1. 23-32 present a comprehensive review of this and other stem cell tissue engineering methods for tendon repair. However, the problems (a) and (b) highlighted above are still valid in the case of functional tissue engineering.

Several efforts have been made to render reconstituted collagen structures with some degree of orientational anisotropy. The alignment of molecules and fibrils by mechanical loading, microfluidic channels, flow and magnetic field induced alignment, electrochemical processing, interstitial flow, high magnetic field, oriented electrospinning, Langmuir-Blodgett deposition, and extrusion processes have been demonstrated in the research lab. The collagen matrices produced by each of these processes have successfully caused the alignment of different cells. However, they do not mimic natural extracellular matrices (ECMs) and lack the essential natural spatial complexity, for example, controlled fibril diameters, aligned fibrils, crimps, periodicity and angular distribution. The lack of secondary structure results in poor strength in the synthetic scaffold and affects cellular survival and behavior. Builles et al. (2007) demonstrate the importance of the cell environment on a newly synthesized ECM. Some have achieved better control of fibril size and demonstrate the formation of tissue-like patterns. However, there are problems with the size of the construct they produce and the lengthy process required. The importance of nano- and micro-structures and their orientation is especially important for tendons and ligaments, since these tissues require strength, elasticity and a guide for cells to attach and migrate for repair to occur. For example, a recent review devoted to cellular-extracellular architecture of human tissue has no discussion about fibril orientation or alignment in ECM, although it states that "the importance of scaffold architecture in tissue engineering is increasingly being realized, which has resulted in a change in trend in the designs of scaffolds, from isotropic scaffolds to heterogeneous and anisotropic "biomimetic" scaffolds, with the goal being to mimic the organization of the cells (such as alignment or clustering) and/or the ECM of the tissue under consideration." See 30. Singh M., Tech B, Berkland C, and Detamore M S. 2008. Strategies and Applications for Incorporating Physical and Chemical Signal Gradients in Tissue Engineering. Tissue Engineering. Part B. 14. 4: 341-366.

More recently, methods to deposit collagen in ordered arrays on glass or plastic substrate to make a thin film with skin-like, tendon-like, aligned-braided, and other fibrillar structures have been described in United States Patent Application Publication No. 2009/0069893 and U.S. patent application Ser. No. 11/951,324, the entire disclosures of which are hereby incorporated by reference. Importantly, these aligned and ordered collagen deposits direct the orientation of cells applied to them. Specifically, cells attach and align on the films and migrate along the axis of alignment. Such films can be treated with factors, such as growth factors which enhance cell survival, migration and proliferation. Other biopolymers can and have been devised to deliver cells to tissues but many lack biocompatibilities, are not lost or incorporated into the tissue or have physical properties quite different from the tissue and alter its function.

Despite substantial efforts to develop biomaterials to mimic tendon, skin and other collagen-based fibrillar tissues, to date there is no industrial manufacturing method for producing these materials. Accordingly, significant further developments are much needed.

SUMMARY OF THE INVENTION

In general, the present invention is related to biocomposite materials and structures, and methods of making and using the same. In some embodiments, the present invention is directed to oriented collagen based biocomposite materials and structures, and methods of making. In some embodiments, methods of forming collagen based films where collagen is arrayed in various forms (aligned, kinked, woven or combinations of the above) are provided. The collagen based films can be converted or formed into individual pseudo-fibers by a sequential application of aqueous solvent and force at a solvent air interface. In some embodiments such pseudo-fibers can be cross linked to enhance their strength as well as treated with various factors or materials such as heparin to enhance their ability to store growth factors and/or to enhance their hydration, among other properties.

In one aspect, embodiments of the present invention provide methods of producing oriented fibrillar biopolymer material comprising the steps of: preparing a fibrillar biopolymer solution or gel of a desired phase; flowing the fibrillar biopolymer solution or gel in a substantially laminar flow regime or manner; and transforming the fibrillar biopolymer solution or gel from a liquid to solid phase to form an oriented fibrillar biopolymer material. In some embodiments the desired phase of the fibrillar biopolymer solution or gel is a liquid crystal phase. In some embodiments the fibrillar biopolymer solution or gel exhibits ionic strength in the range of 0.001M to 0.5M, and a pH in the range of 2 to 9. In other embodiments the ionic strength is in the range of 0.1M to 0.3M, and the pH is in the range of 2 to 5. In some embodiments the step of transforming the fibrillar biopolymer solution or gel to the solid phase comprised drying the solution or gel. Drying may be achieved by a variety of methods such as for example by controlling ambient conditions, such as but not limited to humidity, temperature and electrostatic condition, to promote evaporation.

In some embodiments the fibrillar biopolymer solution or gel is flowed over and deposited on a functionalized substrate. The substrate may be functionalized with any number of desired compounds, such as compounds that promote adhesion, separation, influence the fibrillar organization, and the like.

Of particular advantage, biopolymers according to embodiments of the present invention may be further processed to form biocomposite materials and structures. In one embodiment, an oriented fibrillar material having the form of one or more ribbons is provided. In some embodiments oriented fibrillar biopolymer material are provided having the form of a layer with average fibril orientation in any direction parallel to the layer surface. In other embodiments the layer has an average fibril orientation in the direction perpendicular to the layer surface. In some embodiments fibrillar biopolymer materials are provided having the form of a tube with average fibril orientation either parallel to or having an angle with the tube axis. The oriented fibrillar biopolymer material may have a single crimp pattern. Alternatively, the oriented fibrillar biopolymer material may have a double crimp pattern with an arbitrary angle between crimp formations. In some embodiment the oriented fibrillar biopolymer material exhibits a crimp pattern formed by left-handed and right-handed helical fibrils. In other embodiments, the oriented fibrillar biopolymer material has a crimp pattern in the form of a chevron of substantially parallel lines at substantially equal alternating angles.

In another aspect, embodiments of the present invention provide methods of forming one or more fibrillar biopolymer materials, such as pseudo-fibers, comprising the steps of: dipping a biopolymer material into a solution having substantially neutral pH; and pulling the biopolymer material from the solution such that the material collapses into a pseudo-fiber at an air-liquid interface. The formed fibrillar biopolymer pseudo-fiber may be dried, cross-linked and/or sterilized depending on the desired application.

Of further advantage, the fibrillar biopolymer pseudo-fibers of the present invention may be formed into biocomposite materials and or structures. In some embodiments, a biocomposite structure is provided comprising at least one oriented fibrillar biopolymer material and a biodegradable biocompatible matrix. In other embodiments a biocomposite structure is provided comprising a plurality of oriented fibrillar biopolymer materials with arbitrary orientations, bonded by a biodegradable biocompatible matrix. The biocompatible matrix may be comprised of any suitable material, such as for example with limitation: glycosaminoglycans, proteoglycans, vanadate, calcium phosphates, live cells, growthfactors, and their combinations.

In some embodiments the oriented fibrillar biopolymer material finds use as a matrix and substrate in cell and tissue culture applications. In other embodiments the oriented fibrillar biopolymer material is used as an in vivo cell guiding scaffold. In yet another embodiment the oriented fibrillar biopolymer material comprises a delivery vehicle configured to deliver components to a desired site or target. In one example the material delivers components of platelet rich plasma. In another embodiment the material is configured to deliver live cells for tissue repair and regeneration. In another embodiment the material is configured to deliver peptides, drugs, growth factors, and small molecules.

In some embodiments, the biopolymer materials are made by a liquid film applicator comprising: (i) at least two longitudinal side members having the form of parallel wedge-like rails with their bases occurring in the same plane as the substrate; (ii) a crossover member having the form of a bridge between said side members, wherein said crossover member has at least one flat face and is in contact with each said rail in at least one point; and (iii) a clamp system ensuring strict fixation of the bridge at any preset position on said rails, wherein said bridge can be moved along both said rails so that the flat face of said bridge makes a certain constant dihedral angle within 0-10 arc minutes with the substrate plane and the gap between said flat face and said substrate plane has a width from 5 to 50 microns.

In some embodiments, the biopolymer material is made by the steps of: conveying a collagen solution to a first plate and a second plate, wherein said second plate is held substantially parallel to said first plate at a gap width of 5 to 50 microns, and wherein the collagen solution is captured between said first and second plates; and moving said second plate parallel to said first plate to generate suitable shearing force on said collagen solution to flow the collagen solution in a substantially laminar flow rigeme or manner, wherein said first plate being held stationary during said moving step, and wherein the direction of moving the second plate is the coating direction. In some embodiments, the coating direction is parallel to said uniaxial direction. In some embodiments, the concentration of said collagen solution is about 20 mg/ml-100 mg/ml. In some embodiments, the concentration of said collagen solution is at least 25 mg/ml. In some embodiments, the collagen solution presents in a nematic liquid crystal state. In some embodiments, the collagen layer is made by shearing of concentrated liquid collagen solution.

In some embodiments, the biopolymer solution comprises concentrated liquid collagen solution having at least one of the collagen types of I, II, III, VI and XI, without limitation (including biologically or chemically modified collagen and the like) and optionally having one or more additives, such as for example without limitations an additive that is capable of promoting orientation or adhesion of said collagen. In some embodiments, the additive is ATP.

In another aspect of embodiments of the present invention, threads/sutures/fibers are provided and are found to be suitable as scaffolds for repair and/or regeneration of tissue, and as a cell delivery mechanism. In some embodiments, collagen thread and/or scaffold of the present disclose is produced from a thin ribbon. In some embodiments the ribbon is in the range of about 1-3 μm thick in some embodiments, and about 1-2 μm thick in other embodiments. In some embodiments, the collage thread and/or scaffold is comprised of highly aligned collagen fibrils and has a large surface area suitable for cell ingrowth. In some embodiments the pseudo-fiber has a porous foam-like core. In other embodiments, the collagen pseudo-fiber has a hollow core.

In another embodiment of the present invention, a method of producing a fibrillar biopolymer material is provided comprising the steps of: dipping a thin biopolymer ribbon into a solution with high surface tension, the thin biopolymer ribbon having oriented crimped fibrils; and pulling the biopolymer ribbon along the long axis of ribbon from the solution in the direction of the crimped biopolymeric fibrils orientation such that the ribbon collapses and folds about the long axis of the ribbon at the air-liquid interface as the ribbon is pulled from the solution forming a multilumen fibrillar biopolymer pseudo-fiber wherein the biopolymeric fibrils are aligned along the pseudo-fiber.

In a further aspect, embodiments of the present invention provide a thread-like fibrillar biopolymer (fibrillar biopolymer pseudo-fiber) with a multilumen structure comprising crimped biopolymeric fibrils aligned along the multilumen structure in the direction of the thread-like biopolymer (pseudo-fiber) such that the multilumen structure induces a spontaneous capillary flow of a water-based solution in the pseudo-fiber direction.

BRIEF DESCRIPTION OF THE DRAWINGS

The foregoing and other objects of the present invention will be apparent upon consideration of the following detailed description, taken in conjunction with the accompanying drawings, in which like reference characters refer to like parts throughout.

FIGS. 3A-3F are atomic force microscope (AFM) photographs showing various collagen films or materials formed according to embodiments of the present invention;

FIGS. 12A-1C are photographs depicting human fibroblasts, MSCs, and muscle cells, respectively, on oriented collagen layers to form biocomposite structures according to embodiments of the present invention;

FIG. 18A-E illustrates on example of the thread-like fibrillar biopolymer (fibrillar biopolymer pseudo-fiber): a, b, c—the side view at different magnifications presenting the aligned crimped fibrillar structure; d and e—the cross-sections presenting the multilumen structure.

FIG. 19 is an example of the biocomposite structures comprising an aligned bundle of the pseudo-fibers: A—the aligned bundle of pseudo-fibers encapsulated into a highly porous biodegradable biocompatible matrix (claim 10a); C—the pseudo-fiber; D—the cross-section of the pseudo-fiber; B.1 and B.2—the biocomposite structure comprising an aligned bundle of the pseudo-fibers encapsulated into a tubular biodegradable biocompatible matrix such that the bundle alignment is parallel to the axis of the tubular matrix (claim 10b).

DETAILED DESCRIPTION OF THE INVENTION

Figure 1:
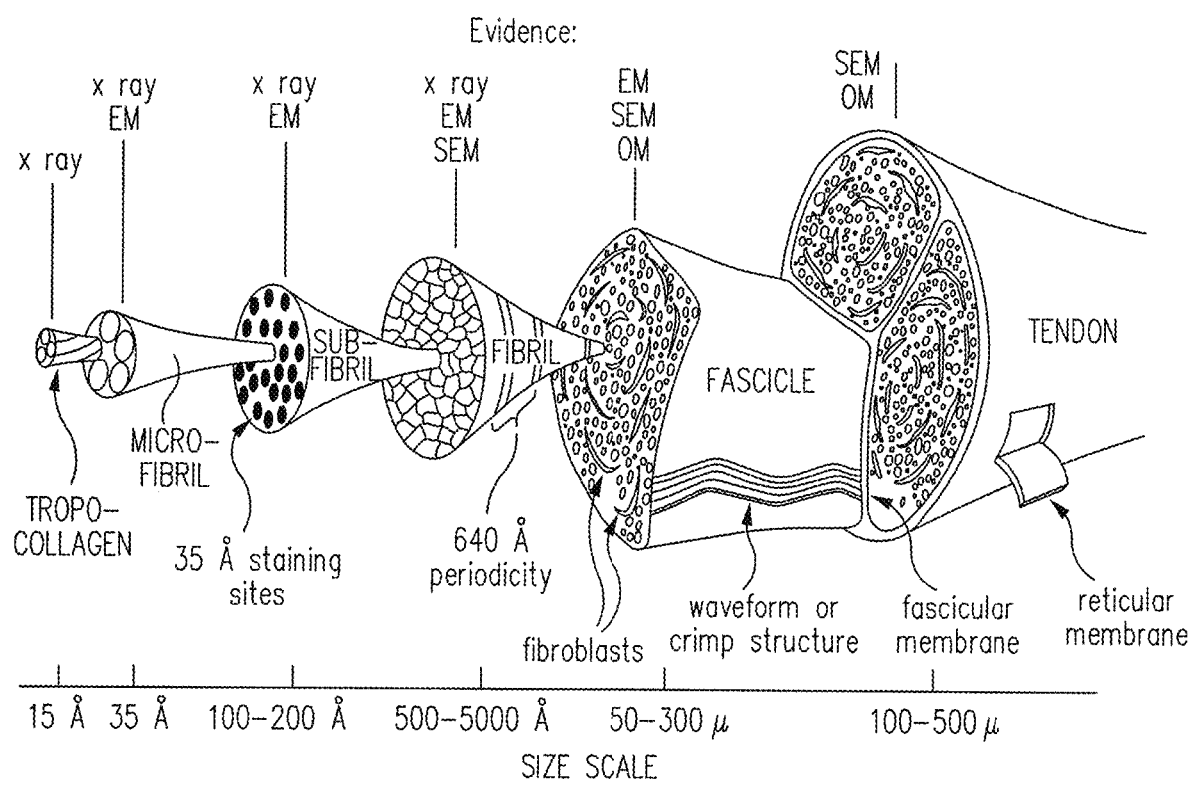
FIG. 1 is a schematic diagram depicting the tendon hierarchy.

It is to be understood that both the foregoing general description and the following detailed description are exemplary and explanatory only and are not restrictive of the compositions, films and methods described herein. In this application, the use of the singular includes the plural unless specifically state otherwise. Also, the use of "or" means "and/or" unless state otherwise. Similarly, "comprise,"

"comprises," "comprising," "include," "includes" and "including" are not intended to be limiting. The terms "layer" or "film" or "thin film" or "matrix" may be used interchangeably throughout the description.

In general, the present invention is related to biocomposite materials and structures, and methods of making and using the same. In some embodiments, the present invention is directed to oriented collagen based biocomposite materials and structures, and methods of making. In some embodiments, methods of forming collagen based films where collagen is arrayed in various forms (aligned, kinked, woven or combinations of the above) are provided. The collagen based films can be converted or formed into individual pseudo-fibers by a sequential application of aqueous solvent and force at a solvent air interface. In some embodiments such pseudo-fibers can be cross linked to enhance their strength as well as treated with various factors or materials such as heparin to enhance their ability to store growth factors and/or to enhance their hydration, among other properties.

The following non-limiting definitions are used herein. "Fibrillar biopolymers" refers to different types of collagen, laminin, fibronectin, fibrin, silk, other polypeptides and their combinations.

"Oriented fibrillar biopolymer material" refers to material which has a repeating pattern. In particular, it can be a crystalline fibrillar biopolymer or semi-crystalline fibrillar biopolymer. In some embodiments the biopolymer is referred to as "oriented" if its surface has a repeating pattern. In particular, the surface pattern can be determined by one of the 17 plane crystallographic groups. The orientation can be assessed by any one of optical polarimetry, polarized microscopy, laser diffraction, x-ray diffraction, atomic probe microscopy, electron microscope.

"Fibrillar biopolymer solution and gel" have different phases depending on the concentration, temperature, pH, ionic strength, and additives. In some embodiments these phases are the liquid crystal phases with long range orientational order (e.g., isotropic, cholisteric, smectic, nematic, hexogonal). Different liquid crystal phases will appear to have distinct textures when viewed under a polarized microscope. Different phase can be recognized by light diffraction and scattering, by Muller matrix polarimetry, by density variation, and by differential calorimetry. Collagen, laminin, DNA, many polypeptides, and other fibrillar biopolymer are the good examples of lyotropic liquid crystal materials. Small amount of inorganic additives (e.g., orthovanadate) may change the phase transition. A comprehensive information on the collagen phase formation is presented in Mosser G, Anglo A, Helary C, Bouligand Y, Giraud-Guille MM. 2006; Dense tissue-like collagen matrices formed in cell-free conditions; Matrix Biology. 25: 3-13, which is incorporated by reference herein in its entirety.

Application of the stable (laminar) flow conditions to a particular liquid phase results in pattern formation. In other words, in some embodiments the biopolymer solution or gel is flowed in a laminar manner or in the laminar regime. Examples of such flow conditions include, but are not limited to: Couette flow, Taylor-Couette flow, plane and axisymmetric Poiseuille flow.

The change of ambient conditions (humidity, temperature, UV, X-ray, e-beam, electric, magnetic field) or key parameters of fibrillar biopolymer like pH and ionic strength may result in self-assembly process and cause transition from liquid/gel phase to a solid phase of oriented material. In an exemplary embodiment the transition from the liquid/gel phase to the solid phase is accomplished by a drying process.

The resulting pattern of the biopolymer in the solid phase is dependent upon the pattern in the liquid phase and the self-assembly process. In one embodiment a fast drying process of the collagen solution results in the formation of helical fibrils with small diameter (transparent material), and a slow drying process results in the formation of helical fibrils with large diameter (hazy material). In the case of a thin collagen layer (e.g., several microns thickness) the resulting orientation substantially depends on the chemical and physical properties of the substrate. In some embodiments functionalization of the substrate may be used to control the orientation.

A "pseudo-fiber" is produced when a free standing ribbon of oriented collagen is caused to roll up lengthwise about the long axis of the ribbon and be held stablely in place by electrostatic forces.

A "thread" is produced by a weaving together a plurality of pseudo-fibers, typically three or more pseudo-fibers.

A "biodegradable matrix" herein refers to a material which can naturally break down and be reabsorbed in a physiological environment. A biocompatible matrix here is a biocompatible material used to bond biopolymers together.

It is useful to briefly review the structure of ligaments and tendons which has been discussed in the literature. While the characteristics of collagen at the molecular level have been extensively studied and are well understood, there is a less clear understanding of the characteristics and structure at the tendon and ligament level.

Some embodiments of the present invention describe a manufactured scaffold product which has the same structure of tendons and ligaments found in mammalian bodies. The method begins with molecular grade collagen, typically type I, and reconstitutes it using a proprietary process into the scaffold. The process creates the scaffold in the absence of cellular or other biological material. Because these additional components are absent, it permits a clearer picture to be obtained of the resulting scaffold and its basic geometric structure. In so doing, it has given insights as to how these parts of the mammalian body are organized and how they are created, which have not been reported to date in the literature.

In describing the structure of ligaments and tendons, there is an organizational hierarchy which has distinct properties at each level. Depending upon how each level is defined, researchers identify six, seven or eight levels. The following table 1 shows the terminology typically used to describe eight levels. (ref: "Tissue Mechanics" by Cowin & Doty, 2007).

TABLE 1

| Level 1 | polypeptide |
| --- | --- |
| Level 2 | tropocollagen |
| Level 3 | microfibril |
| Level 4 | subfibril |
| Level 5 | fibril |
| Level 6 | fiber |
| Level 7 | fascicle |
| Level 8 | tendon and ligament |

Six of the levels, i.e. levels 2, 3, 4, 5, 7, and 8 are shown in FIG. 1. The following explanation is provided to assist the teaching of the present invention. In LEVEL 1, each polypeptide alpha chain which compose the collagen molecule consists of about 1000 amino acid residues. Each chain winds in a left-handed helix about 1.2 nm in diameter.

In LEVEL 2, Tropocollagen or the "collagen molecule" is approximately 300 nm long and 1.5 nm in diameter. It is made up of three polypeptide alpha chains. These three left-handed helices are twisted together into a right-handed coil resulting in a triple helix. This triple helix is a "super helix" since it is right-handed helix comprised three left-handed helices.

In LEVEL 3, The microfibril is formed by five strands of collagen molecules. Each strand is comprised of collagen molecules connected end-to-end with a discrete gap between them. These strands are wound together into a left-handed super-super helix by electrostatic forces to form the microfibril of diameter 3.5 to 4 nm.

In LEVEL 4, The subfibril has a diameter of 10-20 nm and consists of a cluster of microfibrils.

In LEVEL 5, The fibril is formed by winding together subfibrils to make a right-handed super-super-superhelix with a pitch of about 1090 nm and a diameter of 30-500 nm. The gaps between the ends of the collagen molecules of the microfibrils align to form the characteristic 67 nm "D-band" periodicity.

In LEVEL 6, The fiber has a diameter of 1-20 um and consists of a cluster of fibrils.

In LEVEL 7, Fascicles are composed of fibers which are assembled into structures which are organized in a crimp pattern which has been described as undulating waviness, waveform or zigzag. The function of the crimps is to provide the elasticity required for tissues subjected to tensile forces such as ligaments, tendons, heart pericardium, etc. These crimps do not occur in bone collagen that is largely subjected to compression forces. Cellular ingrowth occurs at the fascicle level.

In LEVEL 8, The ligament and tendon are comprised of bundles of fascicles. There is no lateral coupling between fascicles so they can slide freely past each other which creates a smoothly functioning mechanical assembly.

There have been numerous studies on the mechanical behavior of tendons and ligaments, such as the study by A. D. Freed and T. C. Doehring in Freed A. D. and Doehring T. C. 2005; Elastic Model for Crimped Collagen Fibril. J. Biomech. Eng. 127, 587-593. They observed that soft passive tissues are multiconstituent materials that, from a load carrying point of view, are predominantly composed of two elastic substances, collagen and elastin, immersed in a proteoglycan gel. They observe that fascicles are comprised of bundles of fibrils and do not discuss the intermediate form of "fiber". They propose that the crimp formation is tied to the slender aspect ratio of the fibril, which buckles under the internal restoring forces of the elastin matrix whenever a fibrous tissue is free from external load. This rumpled configuration is known as crimp. This invention describes a different mechanism which produces the crimp. It is as a result of a collagen regeneration method as distinct from a buckling phenomena of existing collagen.

As a simplifying assumption, they propose that the fibril which forms the crimp be considered as a mechanical coil spring. This assumption matches well with the observed non-linear stress/strain behavior of crimped collagen tissues wherein the spring exhibits linear behavior at low stresses (toe region) of the stress/strain curve shown in FIG. 2C until the coil becomes stretched out. At that point the coil starts to become stiffer and stiffer causing a continuous increase in the slope of the curve (heel region). After the coil is fully stretched out, the behavior becomes linear again, but at a much steeper slope (linear region). This curve is known as the "J" curve owing to its shape. The mathematical model that they propose matches well with experimental data.

Figure 2A:
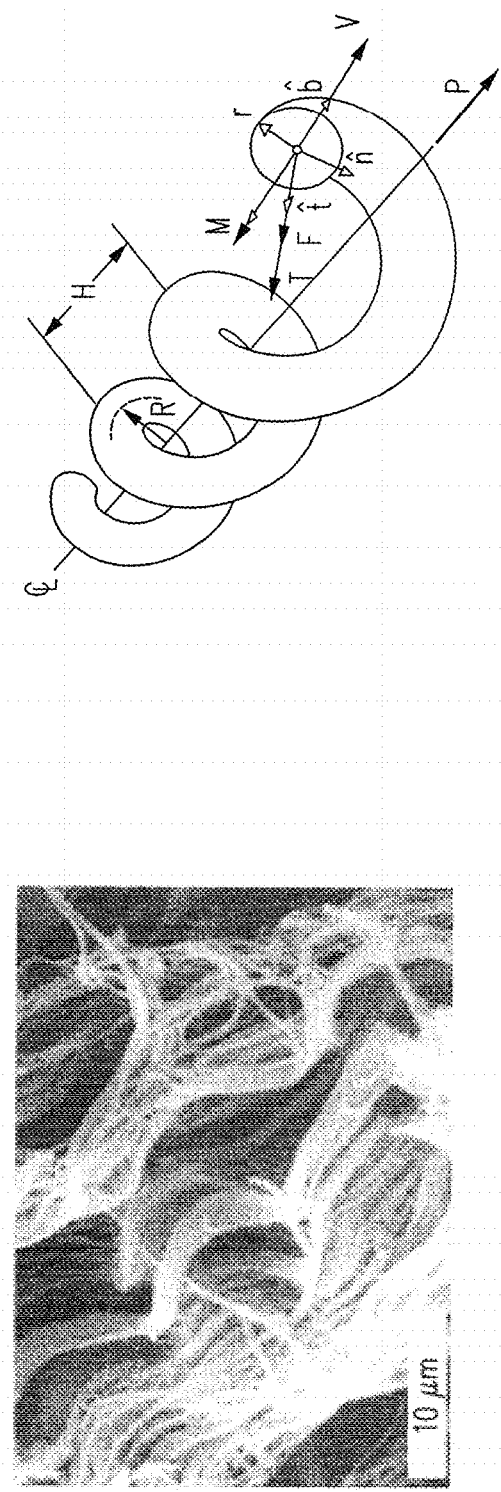
FIGS. 2A-2C show an SEM photograph showing the helical nature of crimped collagen fibers in chordae tendinae taken from a porcine mitral valve, and a diagram of the helical spring used by Freed and Doering in their mathematical model, and the stress stretch curve of the helical collagen fiber, respectively.
Figure 2B:
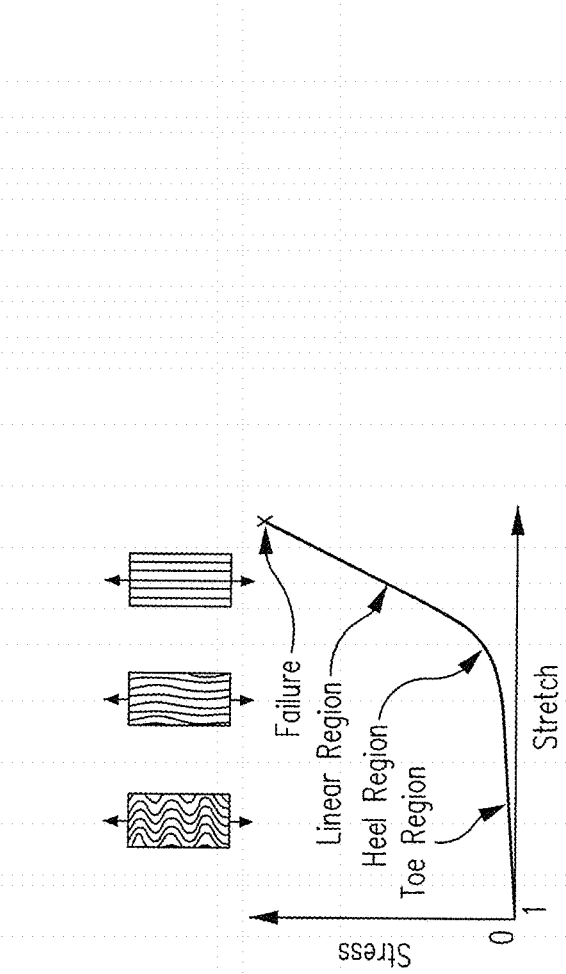
Figure 2C:
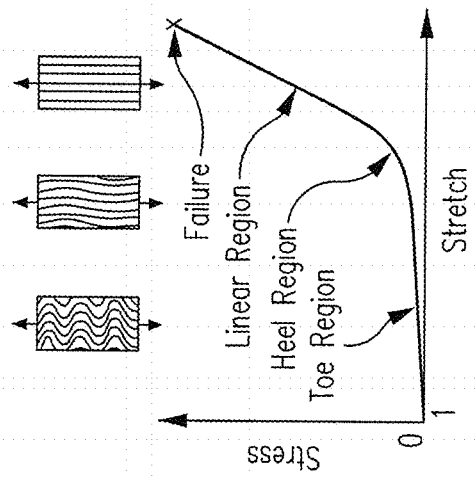

FIG. 2A is an SEM photograph showing the helical nature of crimped collagen fibers in chordea tendinea taken from a porcine mitral valve. FIG. 2B is a diagram of the helical spring used by Freed and Doering in their mathematical model. It shows how the central force acting along the centerline of a helix is transferred to other areas of the helix. Note that the SEM photograph of FIG. 2A shows a left-handed helix while the diagram FIG. 2B shows a right-handed helix. Nowhere in the paper is the difference between the figures noted nor is the concept of handedness discussed, which illustrates a lack of understanding and teaching in the prior art.

While there are many references in the literature to the helical nature of tendon and ligament crimps, no discussion of handedness could be found. Freed and Doering is a specific example of how the notion of handedness has gone unnoticed.

Figure 4A:
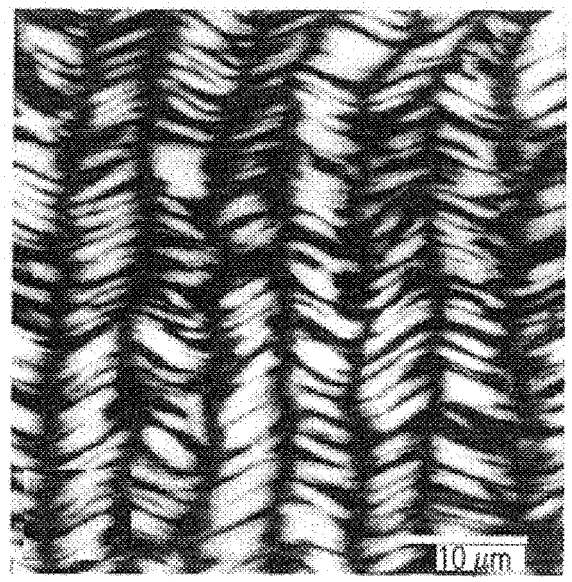
FIGS. 4A-4B are a SEM image of rat-tail tendon, and an AFM image of novel bovine collagen 1 matrix, respectively.
Figure 4B:
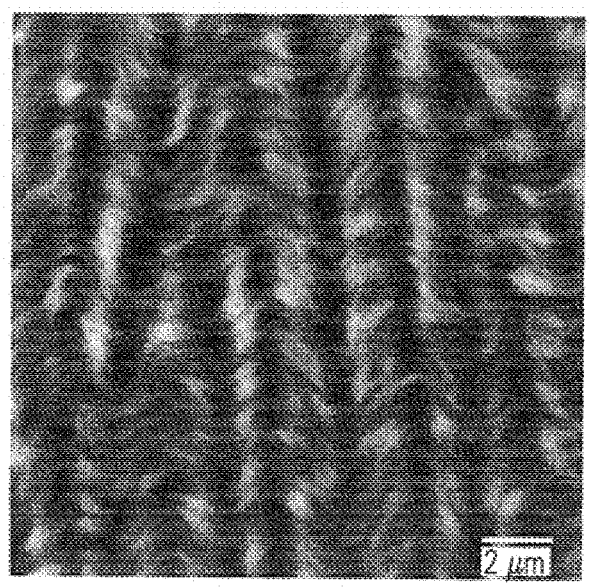

In some embodiments of the present invention are described the production of bioequivalent reconstituted tendon like matrices made from solutions of purified monomeric collagen. These novel matrices include advantages such as but not limited to any one or more of: a) biocompatibility, b) high mechanical strength and "J" elasticity characteristics in the fibril direction, c) defect-free over a large area (2"×10"), d) biomimetic (i.e. approximate the native ligament structure—at the nano- through macro-scales), and e) biodegradable depending on the level of crosslinking. FIGS. 3A to 3F illustrate some examples of collagen films or membranes according to embodiments of the present invention. FIGS. 4A and 4B illustrate a comparison between rat-tail tendon and a collagen matrix formed according to embodiments of the present invention, respectively. The complex crimp and aligned-braided structure of the matrices can incorporate growth factors with a desired spatial gradient to augment biofunctionality. Fibroblasts, myoblasts, neurons, and mesenchymal stem cells show excellent proliferation, migration and alignment on these matrices. The tendon-like matrices can be formed into either fiber structures or multi-layer composite scaffolds. These scaffolds can be repopulated with patient stem cells and factors derived from the patient's platelets to substantially reduce healing time and improve their efficiency. Embodiments of the present invention enable the production of native tissue scaffolds outside of the body.

In one aspect of the present invention, methods of producing a biopolymer material, layer and/or structure are provided. In some embodiments a layer of multidomain semi-crystalline fibrillar biopolymer on a substrate are formed from a predominantly monomeric solution, comprising the steps of: producing a shear flow between a substrate and at least one solid means, inducing a long-range molecular and fibrillar orientation in the solution, controlling initial pH and temperature of the solution, controlling pH and temperature of the solution while in the shear flow, and drying the solution under controlled pH, temperature, and/or evaporation rates of the solution.

The biopolymer layer may be formed of desired orientation. The particular orientation may be characterized by certain parameters and definitions depending upon the biopolymer organization, as discussed in detail below.

In some embodiments the range of orientation is also controlled. Range of orientation is the crystallography term defined as the maximum distance between local domains of same-angle orientation. In this case, the range can be as small as 10 nm for skin-like orientation to as much as 0.5 meter for tendon-like orientation.

Embodiments of the method of the present invention has benefits, such as long-range molecular orientation of liquid crystal solutions with low pH under the shear loading and self-assembly during drying at variable pH. In particular in some embodiments, the drying process can be kept at neutral pH adjusted to 7.4±0.2. The inventors have found that control of pH, temperature, and/or evaporation rate of the solution during the drying process assists in the self-assembly process of the collagen, in addition to applying shear flow.

Different types fibrillar biopolymers can be used: fibrillar collagens, fibronectin, laminin, silk, etc.

Figure 5A:
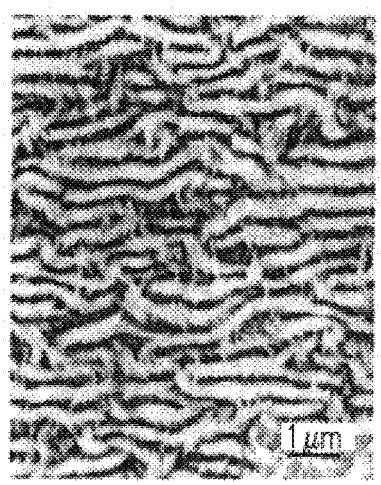
FIGS. 5A-5C are AFM photographs showing various collagen films or materials formed according to embodiments of the present invention.
Figure 5B:
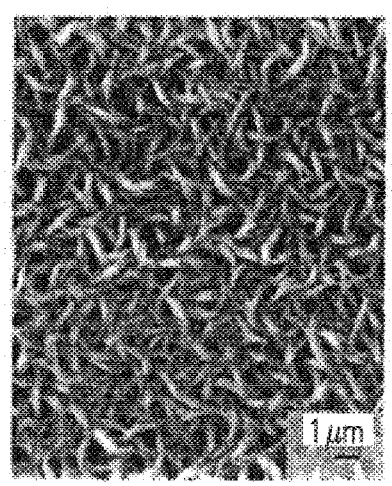
Figure 5C:
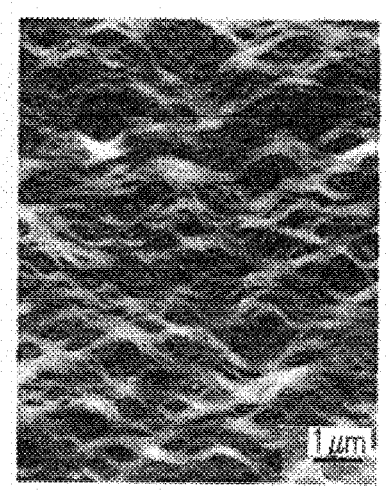

This method enables production of both uniform and multidomain semi-crystalline layers with short and long-range orientations. The distinctions are outlined in Table 2 and shown in FIGS. 5A to 5C.

TABLE 2

| Biopolymer organization | Range of Orientation | Structure |
| --- | --- | --- |
| Tendon-like | Long | Uniform |
| Woven skin-like | Short | Multi-domain |
| Aligned-braided | Long | Uniform |

An example of the collagen layer prepared by the method described above is shown in FIG. 6B. Each fibril extends in a vertical orientation and has a wavy shape which has a characteristic period. The periodicity of adjacent fibrils are approximately equal. The fibrils nest together to create a "crimp" pattern that is formed by the bunching of adjacent fibrils. The crimp pattern lies in the horizontal direction.

Figure 6A:
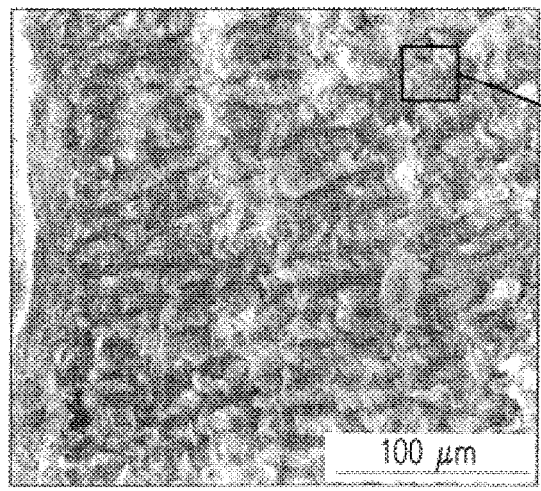
FIGS. 6A-6B are a SEM image of a porcine mitral heart valve, and an AFM image of a tendon like biopolymer matrix according to the present invention, respectively.
Figure 6B:
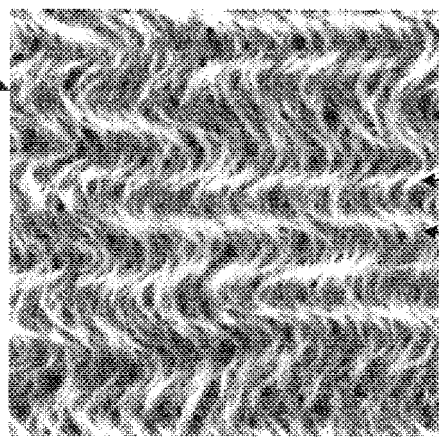

FIG. 6A is an SEM photo of the tendon structure of a porcine mitral heart valve which shows the characteristic crimp pattern seen in all tendons. The area within the box has the same dimensions as the formed material shown in FIG. 6B. It can be seen that the crimp pattern of the artificial matrix in FIG. 6B is similar to the crimp pattern of the actual tendon in FIG. 6A.

The morphology of the crimp pattern described above is formed by the nesting of helical fibrils of collagen. The helical structure is comprised of both right-handed and left-handed helices nested together to form a double super-helix structure as shown with reference to FIGS. 8A to 8C. As shown in the figures, the "darker" shaded fibrils are right-handed, the "lighter" shaded fibrils are left-handed.

Note that the crimps are actually the cluster of peaks of the nested helices. The peaks of the dark helices form right-handed crimps. The peaks of the light helices form left-handed crimps.

These nested helices operate as an array of helical springs. The fact that the array is composed of approximately equal numbers of right and left-handed springs does not affect the spring constant of the array. However when the array is bent rather than extended, the right and left-handed springs tend to balance one another. One side of the array goes into tension, while the other goes into compression. The right and left-handed springs interlock and tend to balance one another creating a natural stability.

Figure 8A:
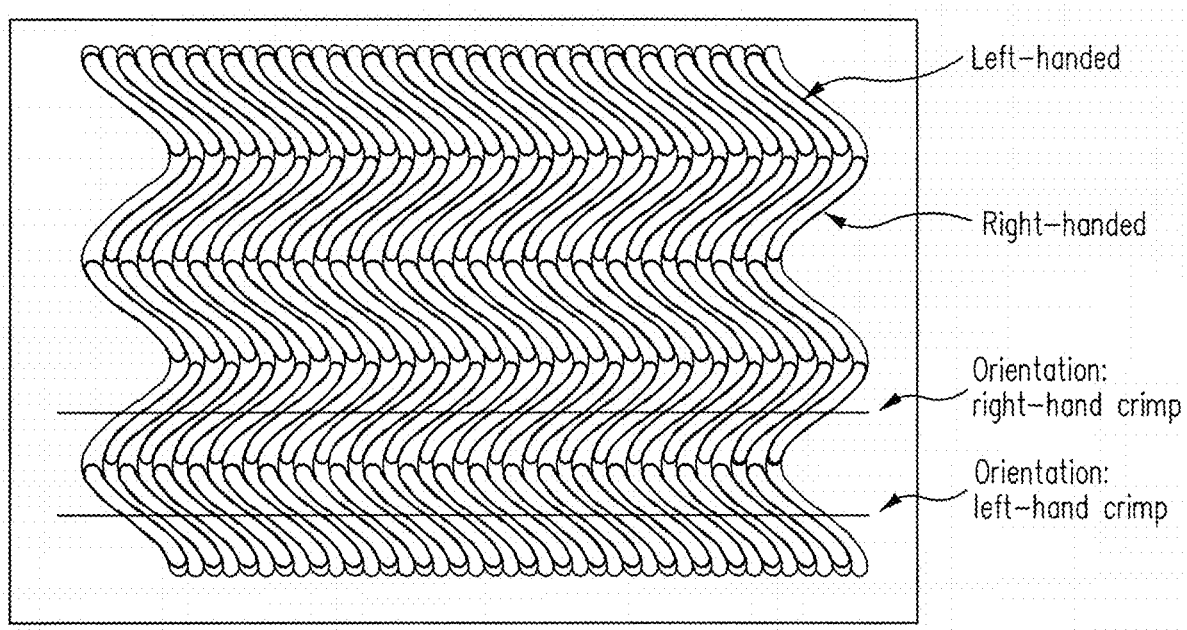
FIGS. 8A-8C illustrate the double super helix structure showing right-handed and left-handed orientation or crimp.
Figure 8B:
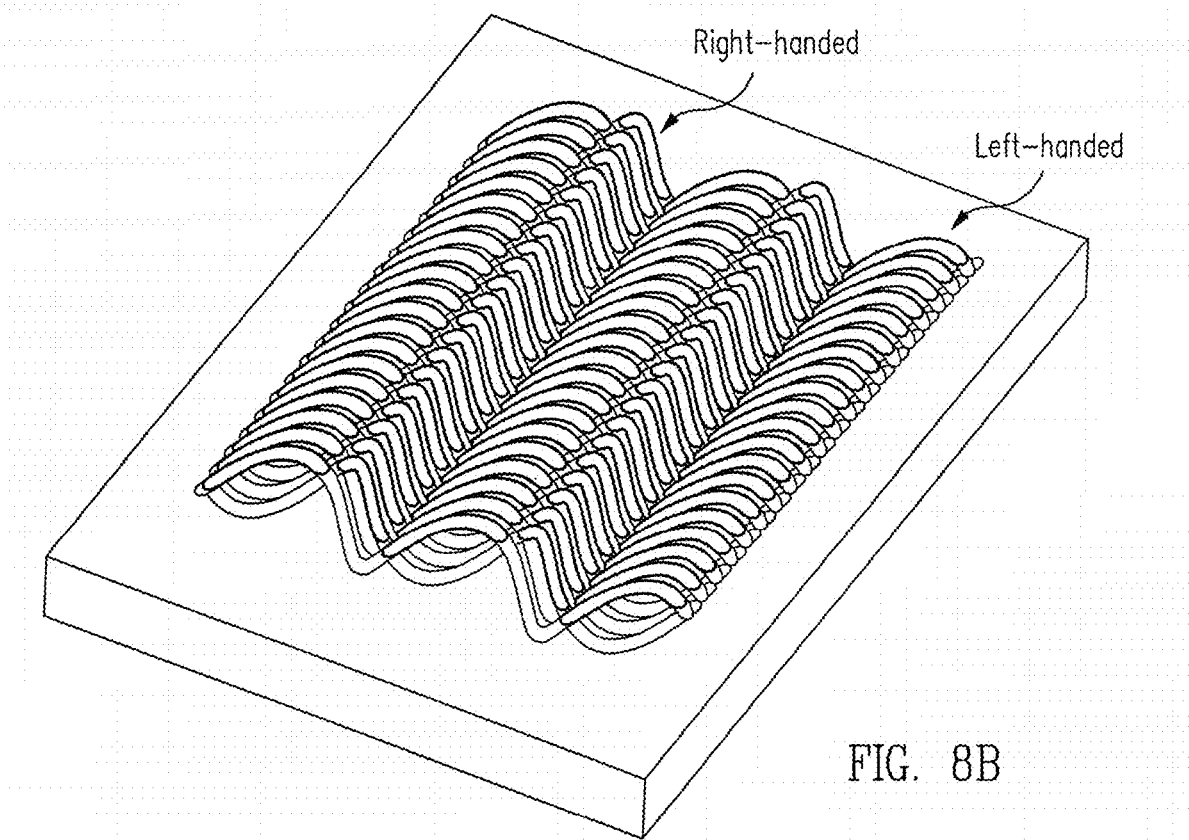
Figure 8C:
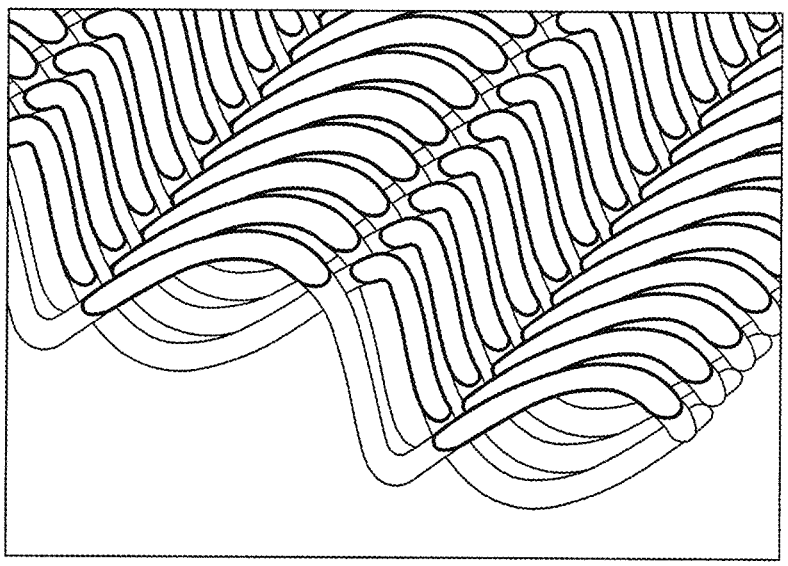

FIGS. 8A-8C show a single double super-helix in several views.

Depending upon the particular biopolymer organization, the definition of "orientation," will have different meanings as illustrated in Table 3 below.

TABLE 3

| Definition of Orientation | | |
| --- | --- | --- |
| Biopolymer organization | Component | Definition |
| Tendon-like | Fibril | Axis of helix |
| Tendon-like | "Crimp" | Line connecting peaks of nested helical fibrils |
| Aligned-braided | Fibril | Axis of helix |
| Woven skin-like | Fibril | Local vector |

Figure 10:
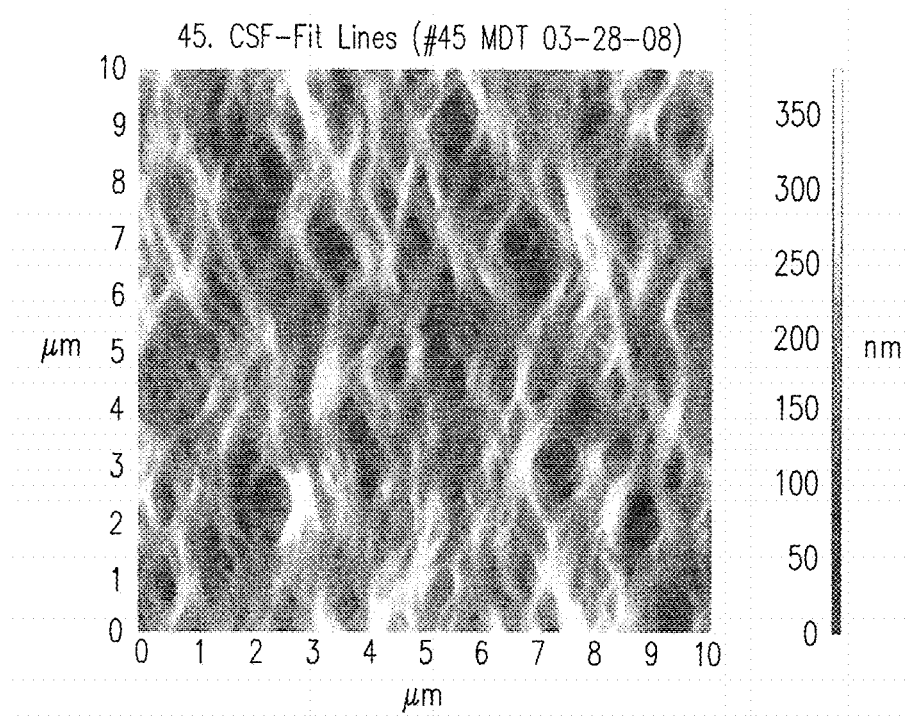
FIG. 10 is an AFM image of a helical, non-nested biopolymer material with aligned-braided orientation according to some embodiments of the present invention.
Figure 11:
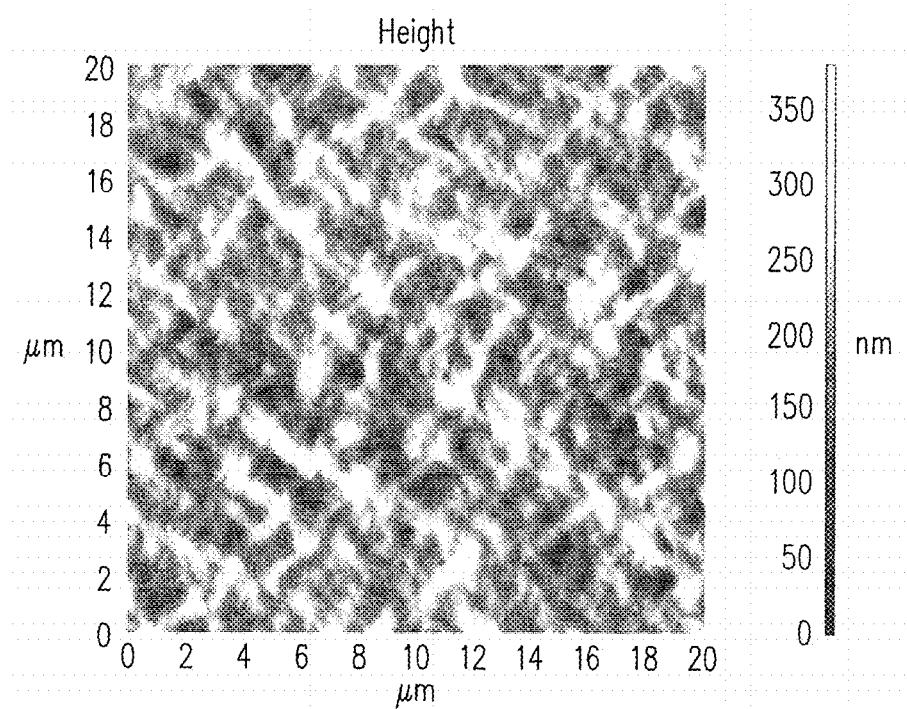
FIG. 11 is a AFM image of a double crimped biopolymer material according to some embodiments of the present invention.

The key difference between tendon-like and the aligned-braided formation shown in FIG. 10 is the packing density of the helices. In the tendon-like, the helices are close-packed, whereas in aligned-braided, the helices are loose-packed. FIG. 11 is an AFM image of a double crimped biopolymer material according to some embodiments of the present invention.

Based upon this more complete understanding of the structure of crimps, the ligament hierarchy can be modified as shown below in Table 4 below.

TABLE 4

| | Description | Helical structure | Structural components |
| --- | --- | --- | --- |
| 1 | polypeptide | Left-handed | 1 alpha chain |
| 2 | tropocollagen | Right-handed | 3 polypeptides |
| 3 | microfibril | Left-handed | 5 tropocollagens |
| 4 | subfibril | | |
| 5 | fibril | Right-handed, left-handed | Clusters of subfibrils |
| 6 | n/a (fiber) | n/a | n/a |
| 7 | fascicle | Right-handed + left-handed | Matched pairs of nested fibrils |
| 8 | tendon and ligament | | |

We have found that these films have oriented fibrillar structure and have some anisotropic mechanical strength and can be removed from the substrate either before or after treatment, modification, neutralization and or cross-linking, and the like.

Figures 12A, 12B, 12C:
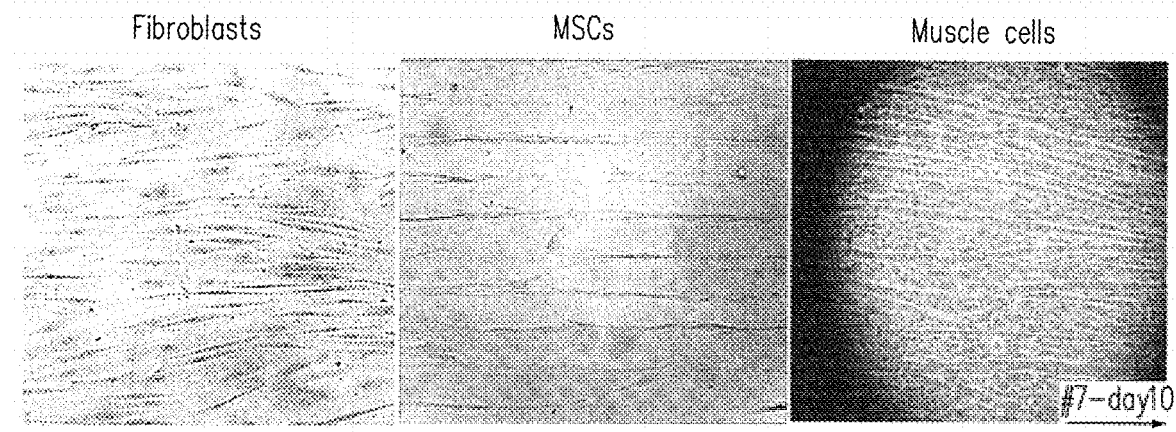

One example of such a modification involves an ion-exchange reaction. For example, it is the treatment by dipping the collagen film in an ortho-vanadate or pyrophosphate solution. Another example is to dip the collagen in a solution of heparin. Such modifications, change the properties of the film such as its ability to be hydrated, its ability to bind proteins or its ability to enhance the behavior of cells applied to it. Some examples of the ability of these collagen matrices to control cell behavior are shown in FIGS. 12A-12C. In general, aligned fibers cause cells to align along their axis. In the case of nerves, while the cells themselves do not show heightened alignment, the neurite processes they produce are highly extended and aligned with the fiber. Such phenomena of matrix structure controlling cell behavior extends to various stem cells.

In some aspects a process for producing tendon-like collagen matrix from purified monomeric collagen solution is provided. Embodiments of this process are suitable for lyotropic liquid crystal materials, among others. According to some embodiments the molecular collagen solution in a liquid crystal state can be deposited on glass and plastic with optical precision by a precision applicator head as shown in and described more fully in U.S. Patent Publication No. 2008/0115724 (and in particular as shown in FIG. 1), the entire disclosure of which is hereby incorporated by reference. In the exemplary embodiment the glass substrate is mounted on a stage which is transported by a linear actuator under a stationary applicator head. The head is adjustable to produce biopolymer matrices of different coating thicknesses. In one example a clean glass substrate and a coating speed of in the range from 10 mm/sec to 1000 mm/sec is used to produce the desired crimp structures. In initial experiments, purified collagen I solutions from any of several commercial sources was used. The resulting matrices can be delaminated from the glass and have a variety of structures in situ as shown in FIGS. 3A to 3F. A three-layer structure can be made comprised of two collagen matrices in cross orientation with a thin heparin layer bonding them together. This sample can be further crosslinked by exposure to riboflavin according to the procedure described in Wollensak G., Wilsch M., Spoerl E., Seiler T. 2004. Collagen fiber diameter in the rabbit cornea after collagen crosslinking by riboflavin/UVA. Cornea. 23. 5: 503-507. Two types of polymers were used, namely dextran and activated PolyEthylene Glycol for crosslinking. The thin tendon-like collagen matrix can be spontaneously converted into a pseudo-fiber as described in more detail below. Preliminary mechanical evaluation of the tendon-like collagen pseudo-fiber (125 µm in diameter) shows strength of at least 60 grams. This construct has considerable strength in both directions even without crosslinking.

Figure 9:
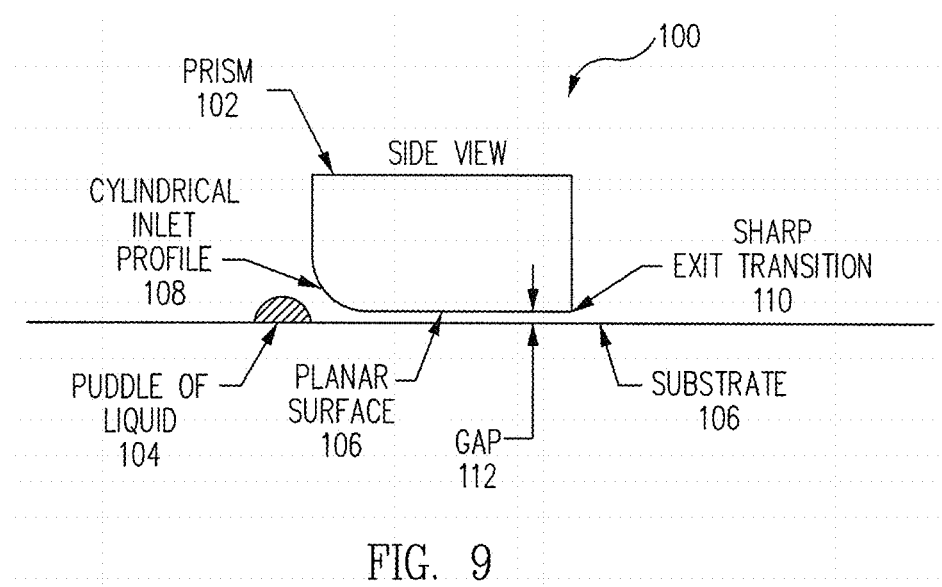
FIG. 9 depicts a schematic diagram of one embodiment of a system, which may be used to carry out methods of the instant invention.

Referring to FIG. 9, another embodiment of the system 100 is shown. In this embodiment, the system 100 may comprise a prism 102 made of a hard material, such as stainless steel and the like. The prism 102 is precisely positioned over a smooth substrate 104, (such as glass, to form a gap 112. Components of the prism 102, in some embodiments, include an inlet profile 108, in some embodiments typically of cylindrical shape, a planar surface 106 polished to a high degree of flatness blended smoothly with the inlet profile and a sharp edge 110 which forms the transition at the exit of the gap 112. The method of positioning the prism over the substrate to form a precise gap is not discussed here. In some embodiments, a narrow strip of collagen solution liquid is deposited on the substrate to form a puddle 114. In certain embodiments, the liquid may be of sufficiently high viscosity to form a free-standing puddle. In some embodiments, the prism is held fixed and the substrate moves from left to right dragging the liquid into the inlet profile zone, causing the liquid to fill the gap until it reaches the exit. The gap can be in the range of 5-50 microns and the coating speed can range from 10 to 100 mm/sec. While in the narrow gap, the liquid is subjected to high shearing forces of sufficient time duration to cause it to become oriented. The sharp edge at the exit serves to minimize the size of the naturally occurring meniscus, which, if too large, would cause unacceptable streaking on the finished film. In alternate embodiments, the prism can be moved in relation to the substrate.

In some embodiments, biocomposites of the present invention are formed using a liquid film applicator comprising: (i) at least two longitudinal side members having the form of parallel wedgelike rails with their bases occurring in the same plane as the substrate ; (ii) a crossover member having the form of a bridge between said side members, wherein said crossover member has at least one flat face and is in contact with each said rail in at least one point; and (iii) a clamp system ensuring strict fixation of the bridge at any preset position on said rails, wherein said bridge can be moved along both said rails so that the flat face of said bridge makes a certain constant dihedral angle within 10 arc minutes with the substrate plane and the gap between said flat face and said substrate plane has a width from 0 to 50 microns.

Other methods of making are also taught according to methods of the present invention. For example, a tubular embodiment is provided wherein the shearing zone has a cylindrical geometry. The cylindrical geometry may be formed by any number of means, and in one embodiment the cylindrical geometry is comprised of a hollow cylinder having positioned within it a solid cylindrical mandrel. The shearing gap is formed by the differences in diameter between the hollow cylinder inner diameter and solid mandrel outer diameter. The biopolymeric material is extruded through the gap under the force of high pressure and in so doing creates a flow such as Couette flow, Taylor-Couette flow, plane or axisymmetric Poiseuille flow to form the oriented scaffold structure. Fine control of the gap can be achieved by fabricating both the hollow cylinder and solid mandrel at a slight taper angle. Axially displacing the mandrel with respect to the hollow cylinder will allow the gap to have a fine adjustment. In the above description, a tube will be formed with the average direction of the fibrils parallel to the central axis of the mandrel and cylinder components. By imparting a differential rotational velocity about the central axis of one component with respect to the other while the collagen tube is being extruded, the average direction of the fibrils will follow a helical path along the tube and create an angle with respect to the central axis.

Figures 7A, 7B:
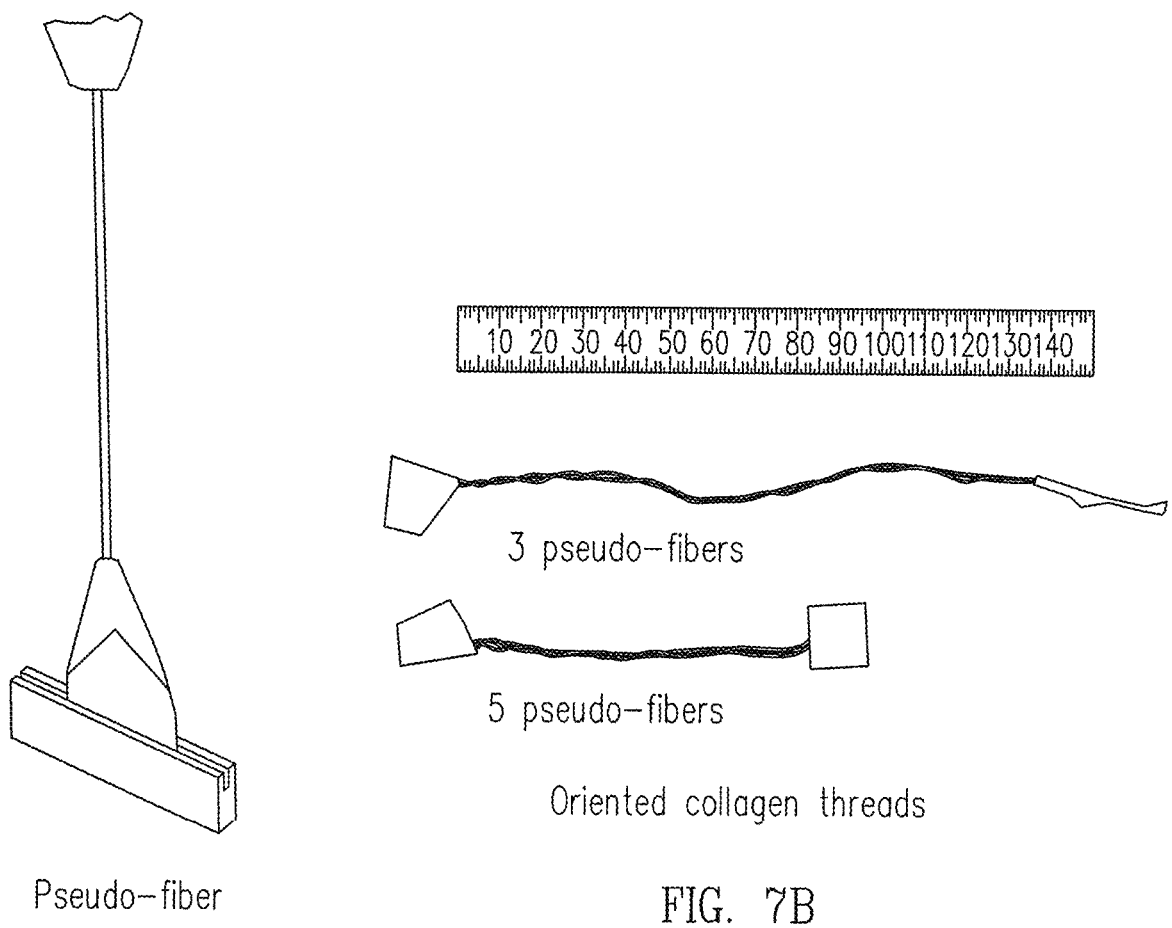
FIGS. 7A-7B are photographs showing a single collagen pseudo fiber, and a collagen thread, respectively, according to embodiments of the present invention.
Figure 13:
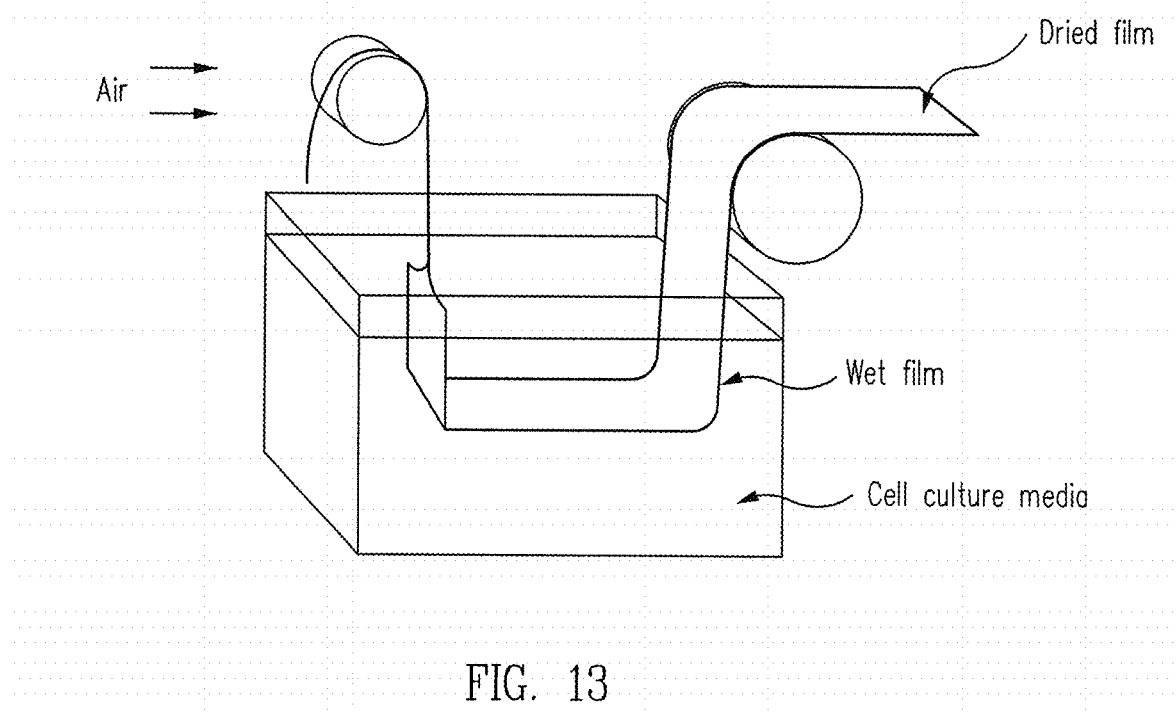
FIG. 13 illustrates a schematic diagram of one embodiment of a system, which may be used to carry out methods of the instant invention to form a pseudo fiber according to embodiments of the present invention.

The discrete or continues biopolymeric film produced as described above can be transferred into the oriented biopolymeric (collagen) pseudo-fiber. This is one of the subjects of the present invention and may be formed by a system such as illustrated in FIG. 13. The thin collagen film (for example, 2-6 um thick and 1" wide) can be fully or partially dipped into a suitable solution as shown in FIG. 13 (for example, PBS solution). The film when removed from the solvent collapses into a pseudo-fiber at the air solution interface as shown in FIG. 7A. The pseudo-fiber can be dried with or without mechanical and thermal treatment. Several pseudo-fibers can be braided to produce threads varying in diameter and strength. Examples of such thread and pseudo-fiber are shown in FIG. 7B. Embodiments of the present invention allow control of the degree of elasticity of the final pseudo-fiber by producing collagen deposits on plastic or glass which have varied arrangement of collagen fibrils. For example, collagen deposited under alternate conditions can produce a kink or fold in the pseudo-fiber and final thread producing a thread with a J type of mechanical extension. Even greater elasticity can be produced by depositing collagen in a woven structure where bundles of aligned fibers support much greater elasticity.

Figure 14:
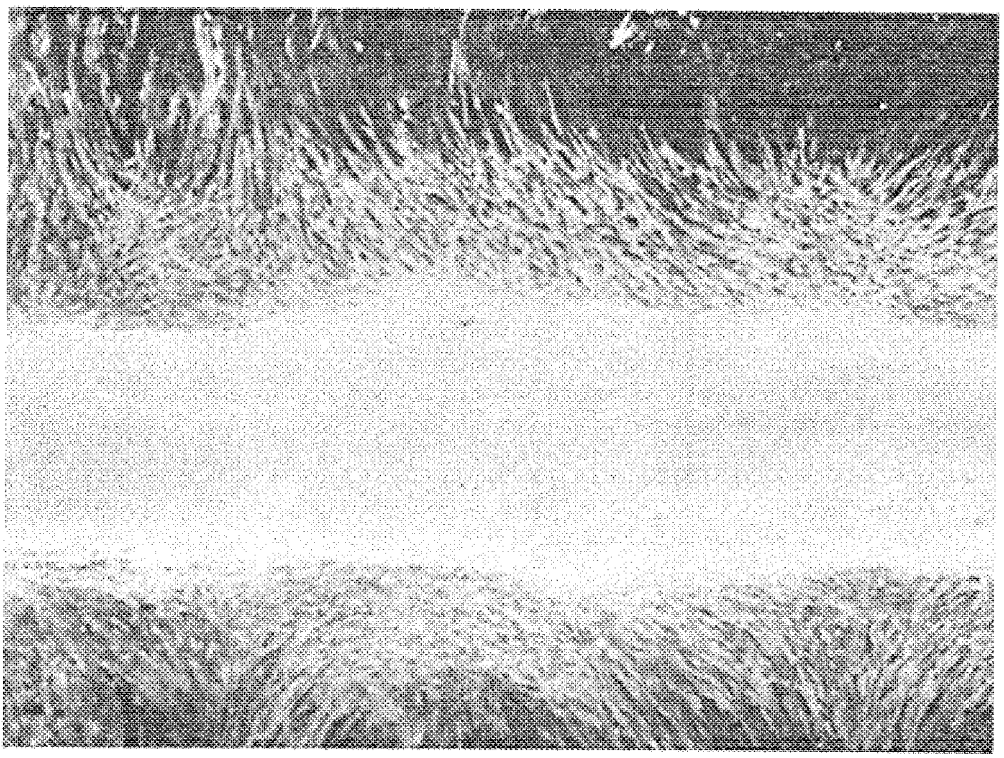
FIG. 14 shows cells seeded on an oriented collagen pseudo-fiber and proliferating and migrating from the pseudo-fiber after five days according to embodiments of the present invention.
Figures 15A, 15B, 15C, 15D:
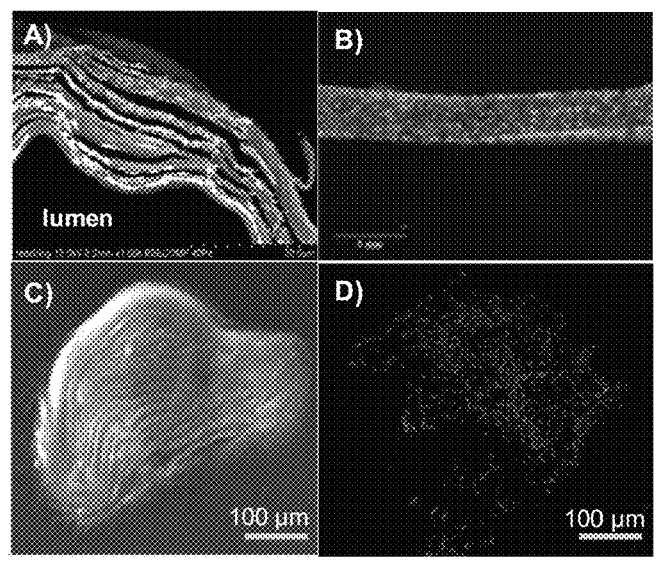
FIGS. 15A-15D are SEM images showing 15A) thread cross-section; 15B) Confluent hMECs, magnification 4×; 15C) Confocal image of thread cross-section; and 15D) Confocal image of hASC populated thread internal cavities (day 3), according to various embodiments of the present invention.

Of particular advantage films, fibers and pseudo-fibers produced according to the present invention may be used to support the attachment, migration and proliferation of cells. In general, cells can be applied to the pseudo-fibers by placing them in a suspension of cells in media. Alternatively, media containing the cells of interest can be applied to the dry suspended pseudo-fiber and allowed to flow down its length. Cells in the media bind to the collagen pseudo-fiber particularly in the presence of serum. The process can be repeated to increase the number of cells bound. One example of the use of oriented collagen pseudo-fiber for the delivery of stem cells into a tissue is shown in FIG. 14.

Typically the cells to be delivered to a specific tissue will be either stem cells, nerve cells, muscle cells, induced pluripotent stem cells, embryonal stem cells or cells expected to improve repair, regeneration or function. Application to tissue can be as a patch or by insertion of a pseudo-fiber into the portion of the injured tissue using a catheter or needle as well known to physicians and those skilled in the art.

Materials such as collagen, laminin, fibronectin or synthetics when deposited on a glass or plastic can serve as a system for testing the response of cells by plating cells thereon and then observing the behavior of the cells, such as whether there is attachment or not of the cells, migration or not, proliferation or not, and the like. Furthermore, growth factors or biological materials such as platelet rich plasma, which is a rich source of factors stimulating cell behavior, can be incorporated into the various substrates. One mechanism that can be used is adsorption. Another is incorporating factors such as heparin or other glycosaminoglycans which bind electrostaticly. Factors can also bind to certain regions of the substrate and have an affinity for a variety of growth factors. Similarly, bioactive materials such as vanadate, anti inflammatory agents of negative charge, or anti proteases including ethylenediamine tetra acetic acid or citrate bind tightly to the positively charged collagen substrates. The ability to modify cell behavior and the ability of cells to degrade the material are readily tested in cell culture. Additionally, such modified substrates are useful in a variety of assays for assessing cell behavior on the modified substrates including nerve cells, stem cells and tumor cells, among others.

Of further advantage, embodiments of the present invention provide methods that enable formation functionalized and/or modified biocomposite structures. In some situations strong adherence to a substrate is required for cell culture studies. This can be accomplished by using functionalized surfaces which bind the deposited biopolymer either ionicly or by covalent bond formation. In other cases where the removal of deposited material is desired various deposition surfaces can be used which allow ready release of the deposit for further processing.

In some embodiments, functional properties of such biopolymers can be modified or improved depending upon the desired application. Such modifications include the cross-linking of the deposited biopolymers and the sterilization of the material as deposited on the substrate or after further manipulations, among others.

In some embodiments collagen starting solutions are prepared as follows. Molecular grade liquid collagen solution is obtained from a number of commercial sources such as BD with concentrations typically in the range of 3 mg/ml. Mammalian sources of the collagen can be rat tail, bovine, porcine, human or others. The solution is placed inside a dialysis membrane tube with molecular weight cutoff range of 12,000 to 14,000 Daltons obtained from Spectrum Labs. The tube is placed in a vessel and covered on all sides with polyethylene glycol (PEG) of a molecular weight 20,000 chilled to 4° C. The PEG molecular weight must be larger than the molecular weight cutoff of the dialysis tube. The vessel and its contents are placed in an environment at 4° C. for a time sufficient for the PEG to remove the water content from the collagen solution and raise its concentration. Times will vary dependant upon the volume of collagen in the tube and the saturation of the PEG on the outside and can be as little as 10 minutes and as much as 3 hours. The concentrated collagen is then removed from the tube and placed into a vial which is centrifuged at 4° C. to remove any entrapped air.

The collagen solution can also be prepared from a powdered form of collagen. Typical method is to add an acid such as HCl or acetic acid at 4° C. to the powder, let sit 18 hours at 4° C. and dilute to the final concentration.

Increased concentration can also be achieved by placing the collagen solution in a commercially designed vial with a dialysis-type membrane mounted at the bottom and centrifuging at 4° C. until desired concentration is achieved. An example of such a vial is Vivaspin manufactured by Sartorius Stedim. Various molecular weight cutoffs of the membrane are available from 10,000 and upwards. Typical final concentrations of the collagen can range from 20 mg/ml up to 100 mg/ml. Preferred concentrations range from 40 mg/ml to 75 mg/ml. and can differ depending upon the desired fibrillar orientation and the particular nature of the starting collagen material from various suppliers.

One important parameter which defines the phase of lyotropic liquid crystals is concentration. The methods to adjust the concentration are described above. Two other important parameters are ionic strength and pH. The used range of pH for liquid collagen I and laminin is from 2 to 9. The preferred range of pH is from 2 to 5. The used range of ionic strength is from 0.001M to 0.5M. The preferred range of ionic strength is from 0.1M to 0.3M.

The standard process of the phase transition is evaporation process which can be accompanied with air-knife drying, vacuum, high and low temperature conditions. For a thin biopolymer layer a UV treatment can be effective if the biopolymer solution has been activated by UV sensitive additive like, for example, riboflavin. In this UV treatment may initiate the biopolymer crosslink.

Self-assembly process in many fibrillar biopolymers highly depends on ionic strength and pH which can be regulated by, for example, ammonia evaporation. In the case of biopolymer deposition on a conductive/metallic substrate the ionic strength can be adjusted by the application of an electric field.

Several polymeric materials like, for example, PET have low adhesion to collagen and laminin therefore this type of material can be used for a surface functionalization if the goal is to remove the oriented biopolymer from substrate. Standard adhesive tape can be used for this procedure.

The aminosilylated glass functionalization causes a substantial change in the structure of oriented collagen thin film deposited on the glass surface. Thus, it results in a vertical fibril formation shown in FIG. 3B instead of skin-like woven pattern shown in FIG. 3D fabricated without glass treatment.

Additionally, certain growth factors, such as insulin, insulin like growth factors, VEGF, PDGF and the like, bind to receptors on the cell surface which stimulate cellular processes through tyrosine kinase receptor domains within the cells. Typically the kinase domain will phosphorylate tyrosine residues on the receptor which puts the receptor in an "active" state. Enzymatic removal of these phosphate residues by certain intracellular phosphatases terminates the "active' state of the receptor and its activity on the cells behavior. Orthovanadate is able to inhibit these phosphatases and enhance receptor phosphorylation and activity.

Factors such as growth factors and orthovanadate can be incorporated into the collagen structures to enhance stability and stimulate cellular responses. Orthovanadate which is incorporated without associated ligand into the actual structure of the collagen matrix secures its retention and minimizes matrix dissolution by serving as an ionic bridge linking adjacent molecules. In this form, the collagen/orthovanadate complex enhances cell matrix interaction and increases cellular responses to endogenous and exogenously added tyrosine kinase growth stimulants especially cell survival, migration, proliferation and differentiation. There are reports of orthovanadate toxicity, however its incorporation in firm ionic association with collagen molecules in the absence of an associated ligand limits the diffusion of orthovanadate, restricts its systemic exposure and limits its actions to cells entering or in contact with the construct.

Of particular significant, threads/sutures/fibers according to embodiments of the present disclosure are found to be suitable as scaffolds for repair and/or regeneration of tissue, and as a cell delivery mechanism. Materials made from type I collagen solution have been researched extensively as scaffolds for repair and regeneration and recently for cell delivery applications (see Enea, D. et al., Extruded collagen fibres for tissue engineering applications: effect of cross-linking method on mechanical and biological properties, J. Mater Sci: Mater Med, 2011, 22, 1569-1578; Cornwell, K. et al., Crosslinking of discrete self-assembled collagen threads: effects on mechanical strength and cell-matrix interactions., J. Biomed Mater Res A., 2007, 80A, 362-71; Zeugolis, D. et al., Cross-linking of extruded collagen fibers-A biomimetic three-dimensional scaffold for tissue engineering applications, J. Biomed Mater Res A., 2009, 89A, 895-908.)

One of the first commercial extruded collagen sutures was manufactured by Ethicon (see Smith, A., Extruded collagen ophthalmic sutures. A clinical survey, Brit. J. Ophthal., 1970, 54, 522-527). Organogenesis further improved the extrusion process (see Kemp, P., et al., Collagen threads, U.S. Pat, No. 5,378,469, 1995). Despite these advancements, the principal aspects of these procedure remain the same and the extruded thread/suture/fiber has a shape of a long compact cylinder with near circular cross-section, and are inadequate in many instances. Limitations are even reported in the literature, for example it is stated that: "The success of these scaffolds has been limited by insufficient tissue ingrowth from the wound margin" (see Cornwell, K. et al., Crosslinking of discrete self-assembled collagen threads: effects on mechanical strength and cell-matrix interactions., J. Biomed Mater Res A., 2007, 80A, 362-71). This is because of the collagen high density and crosslinking treatment used to increase the mechanical properties and decrease the degradation rate of these scaffolds.

In contrast, the novel materials, structures and collagen scaffolds and thread described herein provides advantages and is comprised of a completely different structure. In some embodiments, collagen thread and/or scaffold of the present disclose is produced from a thin ribbon, the ribbon being 1-2 $\mu$m thick in some embodiments. In some embodiments, the collage thread and/or scaffold is comprised of highly aligned collagen fibrils and has a large surface area suitable for cell ingrowth as shown in FIG. 15A-15D.

The scaffold fabrication process is suitable for lyotropic liquid crystal materials. In some embodiments, purified monomeric bovine type I collagen solution was concentrated according to previously published protocols (see Kirkwood, J. E.; Fuller, G. G. Langmuir 2009, 25; 3200-6; Paukshto, M.; McMurtry, D.; Bobrov, Y.; Sableman, E. International Patent application WO/2008/131293; and Bobrov, Y.; Fennell, L.; Lazarev, P.; Paukshto, M.; Remizov, S. *J. Soc. Inf. Display* 2002, 10, 317-321; all incorporated herein by reference in their entirety) to reach a liquid crystal state and sheared onto plastic with optical precision using a liquid film applicator assembly (such as described in McMurtry, D.; Paukshto, M.; Bobrov, International Patent application WO/2008/063631, incorporated herein by reference in its entirety). The method enables control of fibril size, pitch, and helix diameter, as well as membrane thickness. The membrane thickness is controlled by the gap in the coating head and has a typical range of 1-5 $\mu$m. Fibril diameter and alignment were varied by changing pH, ionic strength, collagen concentration, and ambient humidity. Nanofibrillar collagen scaffolds (10 mm long and 0.18 mm in diameters) for in vivo implantation were fabricated by shearing the same liquid crystal collagen solution onto a plastic substrate, delaminating the resulting membrane from the plastic, and converting the free-standing membrane into a scaffold using liquid-air surface tension (as described further in Paukshto, M. V.; McMurtry, D. H.; Martin, G. R.; Zaitseva, T.; Bobrov, Y. International Patent application WO/2010/019625. Conversion of the free-standing membrane (1×25000 $\mu$m cross-section in dry state) into a thread (180 $\mu$m diameter) essentially consists in folding this membrane crosswise, and the resulting thread has multiple interconnected cavities which provide a space for cell attachment and migration.

Figure 16A:
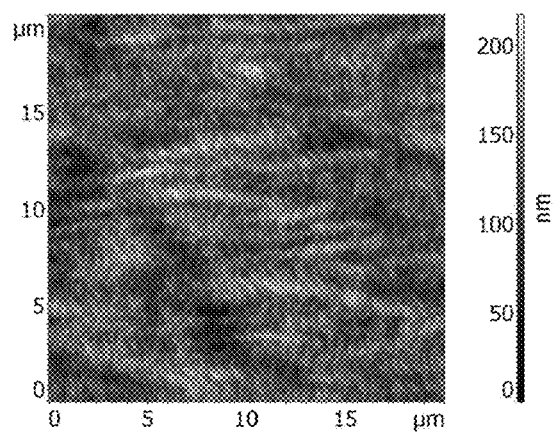
FIG. 16A shows an atomic force microscope (AFM) measurement of a collagen membrane according to some embodiments of the present invention.
Figure 16B:
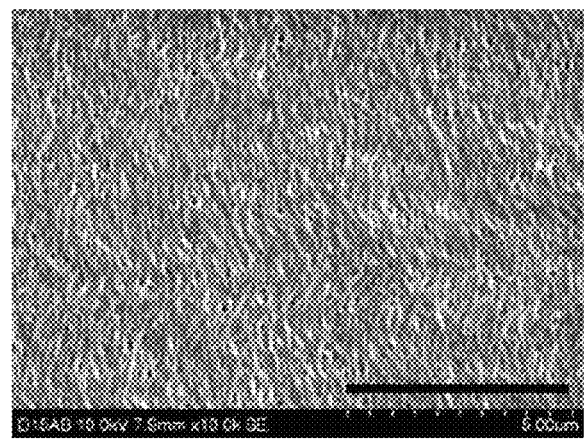
FIG. 16B is a SEM image of a collagen membrane in the environmental (low vacuum) mode according to some embodiments of the present invention.
Figure 17A:
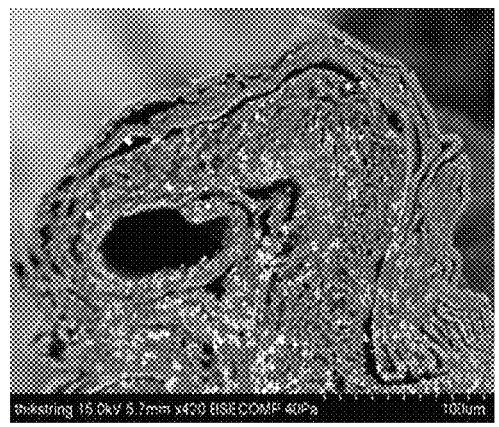
FIG. 17A is a SEM image of a cross-section of a collagen scaffold (e.g. filament/thread) in the environmental (low vacuum) mode according to some embodiments of the present invention.
Figure 17B:
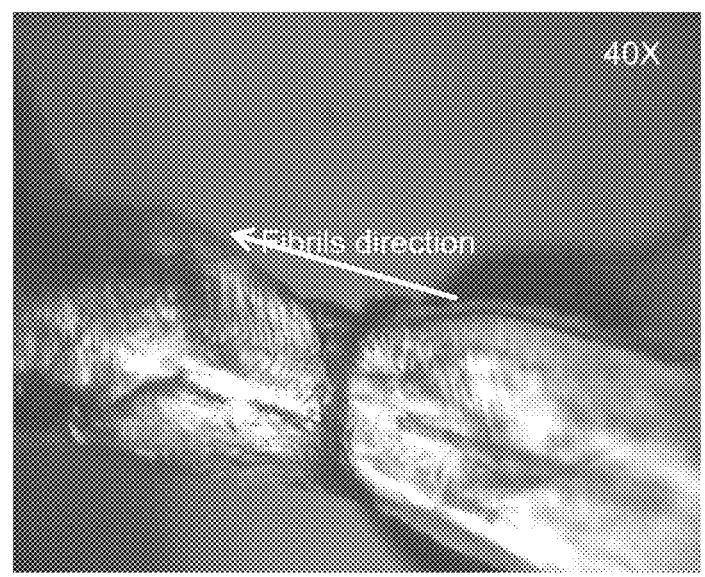
FIG. 17B is a photograph taken by polarized microscope of a collagen scaffold according to some embodiments of the present invention and shown in a wet state under stress just before a break.

AFM and SEM analysis of the Nanoweave collagen membrane on plastic show a nematic structure with highly aligned ~30 nm collagen fibrils as shown in FIG. 16A, and an additional translational order formed by the peaks of helices of the helical-like fibrils ("crimp") (see Bobrov, Y.; Fennell, L.; Lazarev, P.; Paukshto, M.; Remizov, S. *J. Soc. Inf. Display* 2002, 10, 317-321; and Muthusubramaniam, L.; Peng, L.; Zaitseva, T.; Paukshto, M.; Martin, G. R.; Desai, T. A. *J Biomed Mater Res A, Mar* 2012, 100A, (3), 613-621). This crimp is perpendicular to the direction of fibril alignment (FIG. 16A). Collectively, crimps form the "crimp pattern." The crimped configurations of collagen fibrils is typical for collagen-based fibrous tissue when external load is reduced, and mimic the woven spiral structure of collagen bundles in relaxed blood vessels (see Arkill, K. P.; Moger, J.; Winlove, C. P. *J. Anat.* 2010, 216, (5), 547-55). The structure of the collagen fibrils on the plastic substrate was observed using AFM Ntegra Prima and Solver Next (NT-MDT, Santa Clara, Calif.). Images were acquired in the semi-contact mode using silicon tips NSG01 with typical radius <10 nm and spring constant 5.1 N/m (K-Tek Nanotechnology, Wilsonville, Oreg., USA). Corresponding SEM images of the aligned pattern of collagen fibrils measured in the environmental mode using a low vacuum in the specimen chamber is shown in FIG. 16B. After the delaminating the collagen membrane from the plastic and converting it into a thread-like filament (collagen scaffold) its cross-section was measured by SEM as shown in FIG. 17A and polarized optical microscope as shown in FIG. 17B.

We have described methods to prepare purified collagen from solution into films where collagen is arrayed in various forms (aligned, kinked, woven or combinations of the above), among other aspects. Such materials can be converted into individual pseudo-fibers by a sequential application of aqueous solvent and force at a solvent air interface. Such pseudo-fibers can be cross linked to enhance their strength as well as treated with various factors such as heparin and others to enhance their ability to store growth factors and to enhance their hydration. Application to the tissue requiring treatment is by standard procedures well known to physicians skilled in the art.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

EXAMPLES

The following examples are provided for illustration purposes only, and are not intended to limit the scope of the present invention in any way.

Cell culture investigations were performed with fibroblasts and mesenchymal stem cells (mouse adipose-derived and human bone marrow derived). The following cell growth media were used: low-glucose DMEM with 10% FBS for fibroblasts, high-glucose DMEM with 10% FBS for adipose-derived stem cells, alpha-MEM with 20% FBS for human mesenchymal stem cells (all media were supplemented with 1% penicillin/streptomycin and 2 mM L-glutamine).

Example 1

Cell seeding on oriented collagen film (matrix) with tendon-like structure on a glass chip. Fibroblasts and mesenchymal stem cells (mouse adipose-derived and human bone marrow derived) were used. Cells were seeded at 4-6,000 cells/cm$^2$ onto collagen substrates on glass chips placed in 6-well cell culture plates, in growth medium with no FBS and allowed to attach. Then the medium was changed for complete growth medium (with 10% FBS), in which cells were maintained up to one week. The cells align on the substrate according to its pattern, see the FIG. 2A. Cells are observed until they form a monolayer sheet (up to one week).

Example 2 cell seeding on a collagen pseudo-fiber. Fibroblasts were used. Cells were seeded on a oriented collagen pseudo-fiber in a high density cell suspension (10$^6$ cells/ml): a 3-cm pseudo-fiber was placed in an 15-ml Falcon tube with 1 ml of cell suspension and incubated on a shaker for 30 min at 37° C. in CO$_2$ incubator. The cell-seeded pseudo-fiber was then placed into a well of a 6-well culture plate, with its ends fixed with glass chips. Cell attachment was verified after seeding with light microscopy, and cell migration from the pseudo-fiber was monitored with light and fluorescent microscopy, as shown in FIG. 14.

Example 3

Collagen ribbon is dipped into an acidic solution of orthovanadate which has a sodium chloride buffer. As a result of ion-exchange reactions, the orthovanadate will crosslink the collagen fibrils and form collagen-vanadate composite matrix, which preserves the structural characteristics. Neutralization in PBS (Phosphate Buffered Saline) solution and rinsing in DI water removes superfluous orthovanadate.

In another aspect of embodiments of the present invention, threads/sutures/fibers are provided and are found to be suitable as scaffolds for repair and/or regeneration of tissue, and as a cell delivery mechanism. In some embodiments, collagen thread and/or scaffold of the present disclose is produced from a thin ribbon. In some embodiments the ribbon is in the range of about 1-3 μm thick in some embodiments, and about 1-2 μm thick in other embodiments. In some embodiments, the collage thread and/or scaffold is comprised of highly aligned collagen fibrils and has a large surface area suitable for cell ingrowth as shown in FIG. 15A-15D. In some embodiments the pseudo-fiber has a porous foam-like core. In other embodiments, the collagen pseudo-fiber has a hollow core. Experiments and examples for these materials are detailed below.

Example 4

Preparation of a fibrin pseudo-fiber. Fibrinogen from bovine plasma (Sigma, St. Louis) was dissolved in HEPES buffered saline (HBS, 20 mM HEPES, 0.9% NaCl) at 70 mg/mL and stored at −20° C. Thrombin from bovine plasma (Sigma, St. Louis) was stored frozen as a stock solution at a concentration of 40 U/mL in HBS. A coating solution of thrombin was diluted from the stock to a final concentration of 6 U/mL in 40 mM CaCl$_2$ solution. Both the fibrinogen and thrombin solutions were warmed to 37° C., briefly mixed, and deposited on PET by a liquid film applicator (U.S. Pat. No. 8,028,647) with the coating speed of 120 mm/sec. After drying the coated film with thickness about 1 microns having the shape of ribbon was removed from PET. The ribbon was placed on the surface of PBS solution (Sigma, St. Louis) and then gently removed from the solution by pulling up at one side of the ribbon which kept dry. The surface tension of the PBS solution was sufficient to roll the ribbon into the thread-like pseudo-fiber. It is important to have a thin ribbon, preferably an extremely thin ribbon, to achieve the rolling process which transfers or transforms the thin ribbon into a thread-like structure. It is also important to have a ribbon with modest strength in the direction of pulling to withstand the wet weight of the pseudo-fiber. The length of the ribbon that can be transferred into a thread-like pseudo-fiber depends on the strength in the pulling direction. There are two possibilities to increase the length: one is to crosslink ribbon in the dry state (e.g., by UV radiation); other one is to dry pseudo-fiber during the pulling process because the dry strength is about one order of magnitude higher than the wet strength.

Example 5

Preparation of a collagen pseudo-fiber. A similar procedure is used to make the collagen pseudo-fiber from acetic collagen solution (PureCol, Advanced BioMatrix, San Diego, Calif.) as described in Example 4 above. Raw collagen material is concentrated to reach the liquid crystal state (e.g., at 40 mg/ml). Then the concentrated solution is deposited on PET by a liquid film applicator (see U.S. Pat. No. 8,028,647, the disclosure of which is hereby incorporated by reference herein) with the coating speed of 60 mm/sec and applicator gap 30 microns to form an extremely thin ribbon with typical thickness in the range of about 1-3 microns. The long axis of the ribbon coincides with the coating direction and with direction of the collagen fibril alignment. The next steps of the procedure are identical to the steps in the previous example. It is important to pull up the ribbon in the fibril direction by taking it for the dry ribbon tip. PET substrate was used because it has typically low adhesion to the collagen or fibrin. Other fibrillar proteins can be used as soon as they provide a sufficient strength in the pulling direction.

Example 6

Preparation of collagen pseudo-fiber with porous foam-like core. In some embodiments the pseudo-fiber has a porous foam-like core. The procedure to make this pseudo-fiber is similar to the one described in the previous example; however one additional step is the formation of uniform foam layer on the surface of a PBS solution. The collagen foam can be made by high speed mixing of acetic collagen solution (PureCol, Advanced BioMatrix, San Diego, Calif.) with glycosaminoglycan (GAG), e.g., heparin (Celsus, Cincinnati, Ohio). The aqueous dispersion of fibrous cellulose can be used for the foam preparation. Instead of foam a micro-grinded freeze-dried non-soluble collagen can be used to form a thin wet layer on the surface of the PBS solution. Ultrasonic treatment was used to achieve the layer uniformity. The resulting pseudo-fiber has porous core which has been stabilized by cross-linking at 110° C. in a vacuum chamber (less than 50 mbar).

Example 7

Preparation of collagen pseudo-fiber with hollow core. In other embodiments, the collagen pseudo-fiber has a hollow core. To make this structure, triacetate cellulose (TAC) fiber is aligned on the surface of PBS solution along to the long axis of the collagen ribbon. The next steps are similar to the steps in the Example B. The ribbon has to be placed on the surface with the TAC fiber and then pulled up together with TAC fiber such that the TAC fiber is augmented by ribbon. After the drying and crosslinking the TAC fiber is dissolved by acetone. Instead of TAC fiber, a water-soluble cellulose acetate fiber can be used.

In all of Examples 4-7 described above, the PBS solution can be replaced by another solution with sufficient surface tension, e.g., an incubation buffer (135 mM NaCI, 10 mM Tris, 30 mM sodium phosphate dibasic, pH 7.4), and the like.

Example 8

Preparation of biocomposite structure comprising a plurality of the oriented fibrillar biopolymer pseudo-fibers. Several collagen pseudo-fibers are prepared according to the Example 5 and placed between two collagen ribbons formed by aligned collagen fibers prepared from collagen according to methods taught herein, and specifically where the oriented fibrillar biopolymer material is made by method comprising the steps of: preparing a fibrillar biopolymer solution or gel of a desired phase; flowing the fibrillar biopolymer solution or gel in a substantially laminar flow regime or manner; and transforming the fibrillar biopolymer solution or gel from a liquid to solid phase to form an oriented fibrillar biopolymer material, to form a construct. The entire construct is placed under the pressure into a vacuum chamber (vacuum less than 50 mbar) with temperature 110° C. for 72 hours. The resulting structure is suitable for the implantation after e-beam sterilization.

Example 9

Cell delivery by collagen pseudo-fiber with porous core. The pseudo-fiber made according to the Examples 4 and 5 have been used for cell delivery and growth factor delivery applications, however these pseudo-fibers have relatively small surface area and it takes some time to plate the cells. The novel collagen pseudo-fiber with porous core which is made according to the Example 6 has about two orders of magnitude higher surface area and the porous core expresses capillarity effect such that the cell and growth factor suspensions easily fill the porous core. Thus the time to put cells into the novel pseudo-fiber is substantially reduced (from hours to minutes).

Lymphatic Regeneration and/or Repair

Of significant development, embodiments of the pseudo-fiber, threads and scaffolds of the present invention are useful for providing regeneration and/or repair of lymphatic tissue.

The collagen pseudo-fiber prepared according to embodiments of the present invention has various essential natural complexities, including regularly sized aligned fibers, crimps, periodicity and angular distribution. The production process results in bioequivalent scaffolds with controlled 3D nano- and microstructure, pre-determined thickness, fibril size, and high uniformity. These scaffolds can be produced from clinical grade monomeric collagen I in a specific liquid crystal phase under flow conditions, and they are a) biomimetic (i.e. approximating the native tissue structure—at the nano-through macro-scales), b) showing high mechanical strength, c) defect-free over a large area (several $cm^2$), and e) biodegradable depending on the level of crosslinking. Various cell line testing and animal studies indicate that these tissue mimicking devices enable rapid cell attachment, induce cell guidance and aligned cell growth, and are capable of site specific cell delivery. The oriented biopolymer material can be produced as ultrathin (1-5 μm) membranes and are further fabricated into thread-like nanopatterned scaffolds (pseudo-fibers), using liquid-air surface tension the latter can also be braided into multifiber threads. These novel materials present an opportunity to deliver autologous and allogeneic human cells for regeneration purposes. For example, the scaffolds can be used as cell carriers and delivered to a specific site to promote regeneration.

The pseudo-fiber and the biocomposite structure according various embodiments of the present invention can be used for directional regeneration of lymphatic vessels after intradermal or subcutaneous implantation into a subject. For example, the scaffold (thread or bundle of threads) of the present invention can be fit under the skin from puncture sites by a guided needle or trocar. The treads provide the guidance, migration and alignment for lymphatic endothelial and other cells and induce reconnection of disrupted lymphatic system. Additional growth factors like VEGF-C and VEGF-D included in the threads may further speed-up the integration of lymphatic system. Device bridges lymphatic system through a dense scar tissue under the arm that may be "clogging up" the lymphatic channels and preventing fluid circulation.

The device for delivery of the scaffold may be comprised of a guided trocar/catheter containing the scaffold. The first step of the implantation procedure is the introduction of the catheter with the device into a body by a guided trocar/needle from a puncture site. Then the scaffold is anchored and catheter is withdrawn, leaving scaffold behind. The puncture sites may be closed by fibrin/collagen glue and sutured to avoid the formation of lymphocutaneous fistula.

An experiment has been conducted with nanoweave collagen thread cross-linked by 1% genipin for 24 hours (210-μm diameter in dry state). The thread wetted during 15 minutes in PBS (400-μm diameter in wet state) was used as a suture in a fresh chicken leg. The measured maximum pulling force did not exceed 60 g, and the stress applied to the cross-section area of the wet thread was calculated as 5 MPa.

Another important application is the delivery of cells and growth factors into a ischemic mammal leg for treatment of critical limb ischemia. Current cell delivery systems have critical limitations: inefficient cell retention and lack of targeted localization. Collagen, fibrin, gelatin, alginate, and matrigel have been studied as cell delivery vehicles in the form of injectable gels or three-dimensional scaffolds. While many of these materials have shown potential for success, they are not without their limitations. The issue of cell and material retention in injectable gels, as well as vascularization and nutrient diffusion in three-dimensional scaffolds, remains a challenge. The fibrin microthreads proposed recently by Cornwell and Pins have overcome these problems, but they have low mechanical strength and high degradation rate. Advantages of the thread-like scaffolds of the present invention include, but are not limited to: large surface area for cell attachment due to their open, multi-luminal structure; extended survival and maintenance of cells implanted on the threads; the aligned fibers directing cell alignment and migration; tunable mechanical properties to achieve the desired function and persistence. Purified medical grade collagen with low immunogenicity is used as a starting material. This is a substantial advantage over allografts and xenografts.

In some embodiments a catheter is used for guiding the thread. The catheter may have a mechanical positioning system and can be guided by ultrasound or magnetic means. In some embodiments the catheter may include an external needle which contains the device or thread. In the case of bioactive component delivery (e.g., stem cells) the device can be further protected by removable sheath.

There are a number of different ways to fix the device (e.g., thread) before taking out the catheter and the sheath. For example and without limitation, the device may be fixed by: external needle which keeps the thread by locking into a detent attached to the thread; anchor attached to the thread; rigid inner core which can keep or push the thread and then can be removed. The anchor and detent are made from biocompatible material with required strength.

Additional Methods of Making a Biopolymeric Film and Biopolymeric Bilms Formed Thereby When the thin biopolymeric (collagen) film is lifted from the suitable solution with high surface tension (for example suitable PBS solution) to form the pseudo-fiber, in some embodiments the film is dried. In some embodiments, high surface tension is considered to be a surface tension against air of at least 40 millinewton per meter at 25 degree (° C.) and above. Drying can occur in quiescent air or the drying can be hastened by introducing a flow of dry air or dry gas such as dry nitrogen. The air or gas flow is ideally introduced beginning at the point of emergence of the pseudo-fiber from the solution. The nature of the flow is ideally laminar so as to minimally disturb the pseudo-fiber as it is lifted from the solution. The direction of the flow can be perpendicular to the pseudo-fiber but must be at a sufficiently low velocity so as not to vibrate the pseudo-fiber due to Von Karman vortex shedding. Ideally the direction of flow is parallel to the orientation of the pseudo-fiber.

In some embodiments is desirable to have numerous lumens, gaps and cavities within the pseudo-fiber to allow easy access for the cells. To aid in this goal, the sides and interior the pseudo fiber can be expanded by the introduction of gas or air bubbles introduced into the collapse zone during the formation of the pseudo-fiber. These bubbles can be introduced by passing a gas such as nitrogen through a porous block located beneath the collapse zone. They can also be created by creating a DC voltage differential between a wire grid located beneath the collapse zone and a remote electrode also submerged in the conductive PBS solution. The polarity is selected such that either oxygen or hydrogen bubbles can be created beneath the collapse zone.

In quiescent solution the pseudo-fiber is created by a dynamic folding and collapse of the membrane as it is lifted from the solution. The process tends to be random in nature and creates a pseudo-fiber which tends to have a random folded structure. By introducing a laminar flow in the solution parallel to the long axis of the ribbon and in a direction opposite to the travel of the ribbon, a hydrodynamic force causes the random collapse to be biased in one direction thus causing the pseudo-fiber to be more uniform in cross section. Ideally the solution is recirculated to minimize the working volume.

The structure of the pseudo-fiber can be created in a spiral fashion by having the lifting mechanism rotate about the long axis of the pseudo-fiber as it is being lifted from the solution. The torque of the pseudo-fiber is transmitted to the membrane resting in the solution. This causes the membrane to rotate about the axis of the pseudo-fiber. In order to avoid the membrane from contacting the walls of the vessel holding the solution, the shape of the vessel is in the form of a circular pan the radius of which is greater than the length of the membrane.

In some embodiments is desirable to provide the cells multiple access points and openings to the interstices of the pseudo-fiber. Since the membrane making up the pseudo-fiber is non-porous, access is typically provided by lumens which run axially along the pseudo-fiber. There are also typically many transverse openings or side slots which allow cell access to the interstices of the pseudo-fiber. In order to provide another mode of access, the non-porous membrane can be locally fractured by causing an absorbed gas such as carbon dioxide to rapidly expand thus locally fracturing the membrane. This gas can be introduced in a secondary operation after the pseudo-fiber has been fabricated. In some embodiments, carbon dioxide gas is introduced in the head space above cold water in such a manner as to cause the carbon dioxide to be absorbed into the cold water. This is a common method to create carbonated beverages, however such a method has not been used in this context. The pseudo fiber is placed into the cold carbonated water until it is hydrated. The pseudo-fiber is then placed into a vacuum chamber which is quickly evacuated to cause the both the water vapor and carbon dioxide to rapidly and explosively vaporize causing localized fracturing of the membrane.

The pseudo-fiber is created by dynamic folding and collapse of the membrane as it is lifted from the solution. This collapse occurs in a pseudo-random fashion such that all lumens are not created in a strict linear and axial fashion. While many of the lumens are parallel to one another and equi-spaced, there can be a significant number of interruptions to this organized pattern caused by localized openings, crevices and side slots that can persist for many millimeters. These enlargements of the parallel lumens can have the effect of curtailing axial capillary movement of the water-based solution. However these enlargements provide access to the interior of the pseudo-fiber for the water-based solution and new lumens can be accessed such that capillary flow can occur in multiple directions such as transverse, cylindrical and axial directions.

One example of the fibrillar biopolymer pseudo-fiber (=thread-like fibrillar biopolymer) is presented in the FIG. 18A-E, where the diameter of the pseudo-fiber is 0.3 mm, the crimped fibrils are presented in the FIG. 18*b* and FIG. 18*c*, and the cross-section of the pseudo-fiber is presented in the FIG. 18*d* and FIG. 18*e*. As illustrated, a thread-like fibrillar biopolymer (fibrillar biopolymer pseudo-fiber) is provided with a multilumen structure comprising crimped biopolymeric fibrils aligned along the multilumen structure in the direction of the thread-like biopolymer (pseudo-fiber). The multilumen structure induces a spontaneous capillary flow of a water-based solution in the pseudo-fiber direction.

The example of the biocomposite structures comprising an aligned bundle of the pseudo-fibers is presented in the FIG. 19. The biocomposite structure B.1 and B.2, where the pseudo-fibers and the tubular matrix were made from collagen I had been tested in rat model. The structure was used to regenerate a sciatic nerve after implantation bridging the excised part of the nerve.

To address the significant need for off-the-shelf biomimetic scaffold directing functional skeletal muscle regeneration, we tested the biocomposite structures presented in FIG. 19 combined with minced muscle graft. The layers of the structure A made from collagen I and autologous minced muscle graft were sequentially implanted into the void of a volumetric muscle loss (VML) rat model. At the terminal time point, at 2 months post-VML, the animals underwent maximal in vivo isometric torque testing of the anterior muscle compartments. The results demonstrated a substantial functional regeneration of the damage muscles.

The enhanced version of the structure A (FIG. 19) was loaded with HGF vectors based on modified messenger RNA (HGF mmRNA). Due to both myogenic and angiogenic potency of HGF secreted by cells transfected in the scaffold, the scaffold (1) attracted and activated muscle satellite cells and directed the alignment of myoblasts within the defect site to facilitate seamless integration between healthy and regenerating tissue, and (2) recruited and activated vascular endothelial cells and directed the formation of new capillaries along the myofibrils to guide vascularization of the new muscle tissue. A similar effect has been achieved by using insulin growth factor (IGF) vector (IGF-mmRNA). Both type I and type II insulin growth factors were tested.

The typical pseudo-fiber with 0.3 mm in diameter can deliver 5,000-10,000 cells (e.g., fibroblasts or mesenchymal stem cells) per 10 mm length. The methods described herein can substantially increase the amount of the delivered cells due to a more open structure of the pseudo-fiber's wall.

Several experiments presented in the papers below demonstrated that the collagen pseudo-fiber implanted into a mammal induces a localized directional lymphangiogenesis and angiogenesis in the direction of the pseudo-fiber. The "localized" means that the maximum density of newly developed lymphatic vessels or blood vessels is located within about 200 microns from the surface of pseudo-fiber and there is no detectable change in the lymphatic or blood vessel density at the distance more than 2 mm. The "directional" means that the preferred orientation of the newly developed lymphatic or blood vessels coincides with the pseudo-fiber direction.

Nakayama K H, Hong G, Lee J C, Patel J, Edwards B, Zaitseva T S, Paukshto M V, Dai H, Cooke J P, Woo Y J, Huang N F. Aligned-Braided Nanofibrillar Scaffold with Endothelial Cells Enhances Arteriogenesis. ACS Nano. 9(7):6900-8 (2015).

Hadamitzky C, Zaitseva T S, Bazalova-Carter M, Paukshto M V, Hou L, Strassberg Z, Ferguson J, Matsuura Y, Dash R, Yang P C, Kretchetov S, Vogt P M, Rockson S G, Cooke J P, Huang N F. Aligned nanofibrillar collagen scaffolds—Guiding lymphangiogenesis for treatment of acquired lymphedema. Biomaterials. 2016; 102:259-67.

Adaptive immune responses are induced in vivo or in vitro by stimulation of T and B lymphocytes by antigen-presenting cells, most notably by activated dendritic cells or by combination of dendritic cells and activated T-cell. Induction of antigen-specific immune responses is important in medical applications such as vaccination, where pathogen-derived antigens or recombinant or synthetic antigens are used in conjunction with adjuvant molecules to activate T-cells and dendritic cells. In some embodiments the invention introduces a new method for localized delivery of activated T-cells and dendritic cells where the aligned fibrillar pseudo-fiber (e.g., collagen aligned fibrillar pseudo-fiber) enhances immunotherapeutic effect of the activated cells by localized directional lymphangiogenesis.

T-cells and dendritic cells can be plated on the pseudo-fiber or on the biocompatible matrix and activated before implantation. The cell can also form lymphoid clusters on the surface of the pseudo-fiber before the implantation. The cell delivery using the scaffolds (the pseudo-fiber or the biocompatible matrix) is substantially increase the cell survival in a harsh environment, ensures localized targeted delivery of therapeutic cells or clusters of cells in the area affected by cancer (e.g., solid cancer). The localized directional lymphangiogenesis attracts lymphocytes and endothelial cells to the vicinity of the implanted scaffold where the attracted cells will be further stimulated/activated by the delivered cells. It is important that this secondary activation is highly localized in the cancer affected area where the scaffolds are delivered. This localization can reduce some undesired complications, like autoimmune response to the activated cells.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

All patents, patent applications, publications, and references cited herein are expressly incorporated by reference to the same extent as if each individual publication or patent application was specifically and individually indicated to be incorporated by reference.

We claim:

1. A method of producing a fibrillar biopolymer material comprising the steps of:
   dipping a thin biopolymer ribbon into a solution, the thin biopolymer ribbon having oriented crimped fibrils; and
   pulling the biopolymer ribbon along the long axis of ribbon from the solution in the direction of the crimped biopolymeric fibrils orientation such that the ribbon collapses and folds about the long axis of the ribbon at the air-liquid interface as the ribbon is pulled from the solution forming a multilumen fibrillar biopolymer pseudo-fiber wherein the biopolymeric fibrils are aligned along the pseudo-fiber and wherein the method further comprises:
   drying the fibrillar biopolymer pseudo-fiber with a flow of dry air or dry gas which continuously surrounds the fibrillar biopolymer pseudo-fiber as it is pulled from the solution.

2. The method according to claim 1 wherein the ribbon collapses and folds about the long axis of the ribbon forming the multilumen structure comprising of the crimped biopolymeric fibrils aligned along the multilumen structure in the direction of the pseudo-fiber such that the multilumen structure induces a spontaneous capillary flow of a water-based solution in the pseudo-fiber direction.

3. The method according to claim 2 further comprising: cross-linking the fibrillar biopolymer pseudo-fiber.

4. The method according to claim 3 wherein the fibrillar biopolymer pseudo-fiber is further used to deliver cells, peptides, drugs, growth factors, small molecules, nucleic acids, or artificial nucleic acid analogues.

5. The method according to claim 4 wherein the delivery is used for tissue repair and/or regeneration and/or modification.

6. The method according to claim 3 further comprising:
forming a biocomposite structure comprising a plurality of the fibrillar biopolymer pseudo-fibers with arbitrary orientations.

7. The method according to claim 3 further comprising:
forming a biocomposite structure comprising an aligned bundle of the pseudo-fibers encapsulated into a porous biodegradable biocompatible matrix.

8. The method according to claim 7 wherein the porous biodegradable biocompatible matrix has an elongated porous structure aligned along to the bundle alignment.

9. The method according to claim 7 wherein the biocomposite structure comprising: an aligned bundle of the pseudo-fibers and a tubular biodegradable biocompatible matrix such that the bundle alignment is parallel to the axis of the tubular matrix.

10. The method according to claims 6 or claim 8 wherein the biocomposite structure is used for directional regeneration of a muscle tissue after implantation into a subject.

11. The method according to claims 4 or claim 9 wherein the biocomposite structure is used for directional regeneration of a nervous tissue (neural tissue or nerve tissue) after implantation into a subject.

12. The method according to claim 8 wherein the biocompatible matrix further comprising: at least one of collagen, fibronectin, fibrin, laminin, glycosaminoglycans, proteoglycans, vanadate, calcium phosphates, live cells, growth-factors, nucleic acids, or artificial nucleic acid analogues, and their combinations.

13. The method according to claims 3 or claim 8 wherein the fibrillar biopolymer pseudo-fiber and the biocomposite structure is used for directional regeneration of lymphatic and blood vessels after implantation into a subject.

14. A method of producing a fibrillar biopolymer material comprising the steps of: dipping a thin biopolymer ribbon into a solution, the thin biopolymer ribbon having oriented crimped fibrils; and pulling the biopolymer ribbon along the long axis of ribbon from the solution in the direction of the crimped biopolymeric fibrils orientation such that the ribbon collapses and folds about the long axis of the ribbon at the air-liquid interface as the ribbon is pulled from the solution forming a multilumen fibrillar biopolymer pseudo-fiber wherein the biopolymeric fibrils are aligned along the pseudo-fiber and wherein a stream of gaseous or air bubbles is introduced into the solution beneath the zone of collapse and folding such that the gaseous or air bubbles rise up and a portion of the gaseous or air bubbles are encapsulated within the folds of the ribbon as it collapses.

15. A method of producing a fibrillar biopolymer material comprising the steps of: dipping a thin biopolymer ribbon into a solution, the thin biopolymer ribbon having oriented crimped fibrils; and pulling the biopolymer ribbon along the long axis of ribbon from the solution in the direction of the crimped biopolymeric fibrils orientation such that the ribbon collapses and folds about the long axis of the ribbon at the air-liquid interface as the ribbon is pulled from the solution forming a multilumen fibrillar biopolymer pseudo-fiber wherein the biopolymeric fibrils are aligned along the pseudo-fiber and wherein the solution flows in a laminar fashion substantially parallel to the long axis of the biopolymer ribbon and in a direction opposite to the linear motion of the biopolymer ribbon.

16. A method of producing a fibrillar biopolymer material comprising the steps of: dipping a thin biopolymer ribbon into a solution, the thin biopolymer ribbon having oriented crimped fibrils; and pulling the biopolymer ribbon along the long axis of ribbon from the solution in the direction of the crimped biopolymeric fibrils orientation such that the ribbon collapses and folds about the long axis of the ribbon at the air-liquid interface as the ribbon is pulled from the solution forming a multilumen fibrillar biopolymer pseudo-fiber wherein the biopolymeric fibrils are aligned along the pseudo-fiber wherein the fibrillar biopolymer pseudo-fiber is rotated about the long axis of the fibrillar biopolymer pseudo-fiber as the ribbon is pulled from the solution.

17. The method according to claim 1 wherein the fibrillar biopolymer pseudo- fiber is hydrated in a liquid containing dissolved carbon dioxide or other dissolvable gas and at a temperature sufficient to keep the carbon dioxide or other dissolvable gas from coming out of solution and the fibrillar biopolymer pseudo-fiber is subsequently placed into a chamber wherein a vacuum is created at a rate such that the carbon dioxide or other dissolvable gas comes out of solution to create bubbles of sufficient size to cause localized fracturing of the walls of the fibrillar biopolymer pseudo-fiber.

18. The method according to claim 4 wherein the cells include an immunotherapeutic activated T-cells or dendritic cells or their combination for treatment of solid cancer or cancer metastasis such that at least one fibrillar biopolymer pseudo-fiber induces localized lymphangiogenesis in a vicinity of the pseudo-fiber and enhance the immunotherapeutic effect of the activated cells after implantation of the pseudo-fiber with the plated cells into a human subject.

19. The method according to claim 12 wherein the cells include an immunotherapeutic activated T-cells or dendritic cells or their combination for treatment of solid cancer or cancer metastasis such that at least one fibrillar biopolymer pseudo-fiber induces localized lymphangiogenesis in a vicinity of the pseudo-fiber and enhance the immunotherapeutic effect of the activated cells after implantation of the biocompatible matrix into a human subject.

\* \* \* \* \*